United States Patent [19]

Kiefer et al.

[11] Patent Number: 5,750,660
[45] Date of Patent: May 12, 1998

[54] BICYCLOPOLYAZAMACROCYCLOPHOSPHONIC ACID HALF ESTERS

[75] Inventors: Garry E. Kiefer, Lake Jackson; Jaime Simon, Angleton; Joseph R. Garlich, Lake Jackson, all of Tex.

[73] Assignee: The Dow Chemical Company, Midland, Mich.

[21] Appl. No.: 683,653

[22] Filed: Jul. 15, 1996

Related U.S. Application Data

[63] Continuation of Ser. No. 58,101, May 6, 1993, abandoned, which is a continuation-in-part of Ser. No. 805,551, Dec. 10, 1991, abandoned.

[51] Int. Cl.$^6$ .................................................. C07F 13/00
[52] U.S. Cl. .......................... 534/10; 534/14; 424/1.11
[58] Field of Search ...................... 540/472; 424/1.77, 424/1.11, 1.65; 534/10, 14, 15, 16

[56] References Cited

U.S. PATENT DOCUMENTS

| | | | |
|---|---|---|---|
| 4,156,683 | 5/1979 | Lehn | 260/338 |
| 4,639,365 | 1/1987 | Sherry | 424/9 |
| 4,647,447 | 3/1987 | Gries et al. | 424/9 |
| 4,822,594 | 4/1989 | Gibby | 424/9 |
| 4,877,600 | 10/1989 | Bonnemain et al. | 424/4 |
| 4,885,363 | 12/1989 | Tweedle et al. | 540/465 |
| 4,889,931 | 12/1989 | Rocklage et al. | 540/465 |
| 4,920,195 | 4/1990 | Kankare et al. | 534/16 |
| 4,923,985 | 5/1990 | Gansow et al. | 540/474 |
| 4,940,796 | 7/1990 | Mathias et al. | 546/323 |
| 4,957,939 | 9/1990 | Gries et al. | 514/492 |
| 4,963,344 | 10/1990 | Gries et al. | 424/9 |
| 4,986,980 | 1/1991 | Jacobsen | 424/9 |
| 5,026,802 | 6/1991 | Mathias et al. | 526/259 |
| 5,047,527 | 9/1991 | Handel et al. | 540/474 |
| 5,049,667 | 9/1991 | Schaefer et al. | 540/474 |
| 5,053,503 | 10/1991 | Dean et al. | 540/474 |
| 5,059,412 | 10/1991 | Simon et al. | 424/1.1 |
| 5,236,695 | 8/1993 | Winchell et al. | 424/9 |
| 5,318,772 | 6/1994 | Frank et al. | 424/49 |
| 5,320,829 | 6/1994 | Garlich et al. | 424/54 |
| 5,322,681 | 6/1994 | Klaveness | 424/9 |
| 5,334,371 | 8/1994 | Gries et al. | 424/9 |
| 5,385,893 | 1/1995 | Kiefer | 514/80 |
| 5,428,139 | 6/1995 | Kiefer et al. | 534/10 |
| 5,480,990 | 1/1996 | Kiefer et al. | 540/465 |
| 5,645,818 | 7/1997 | Jackels et al. | 424/9.363 |

FOREIGN PATENT DOCUMENTS

| | | | |
|---|---|---|---|
| 0238196 | 9/1987 | European Pat. Off. | A61K 49/00 |
| 0352218 | 1/1990 | European Pat. Off. | |
| 0391766 | 10/1990 | European Pat. Off. | |
| 391766 | 10/1990 | European Pat. Off. | |
| 0430863 | 6/1991 | European Pat. Off. | |
| 0438206 | 7/1991 | European Pat. Off. | |
| 9110669 | 10/1990 | WIPO. | |
| 9110645 | 7/1991 | WIPO. | |
| 91/10645 | 9/1991 | WIPO. | |

OTHER PUBLICATIONS

Greene. *Protective Groups in Organic Synthesis*, John Wiley & Sons, pp. 10–17, 1981.
Chemical Abstracts, vol. 113, (1990), p. 701, Abstract No. 59139g.
Chemical Abstracts, vol. 115, (1991), p. 21, Abstract No. 280870b.
Chemical Abstracts, vol. 115, (1991), p. 585, Abstract No. 58294h.
Chemical Abstracts, vol. 115, (1991), p. 845, Abstract No. 20829y.
Chemical Abstracts, vol. 115, (1991), p. 938, Abstract No. 183387s.
Chemical Abstracts, vol. 116, (1992), p. 583, Abstract No. 21083h.
Derwent Publications. Ltd., Abstract No. 85–018012/03. Mar. 25, 1983.
Derwent Publications, Ltd., Abstract No. 87–229593/33. Jan. 23, 1986.
Derwent Publications, Ltd., Abstract No. 87–250202/35. Feb. 13, 1986.
Derwent Publications, Ltd., Abstract No. 90–099224/13. Aug. 24, 1988.
Derwent Publications, Ltd., Abstract No. 90–307139/41. Mar. 24, 1989.
Derwent Publications, Ltd., Abstract No. 91–216892/30. Jan. 18, 1990.
Chemical Abstracts, vol. 74, (1974), p. 476, Abstract No. 60361f.
Chemical Abstracts, vol. 95, (1981), p. 702, Abstract No. 115487t.
Chemical Abstracts, vol. 100, (1984), p. 593, Abstract No. 209772f.
Chemical Abstracts, vol. 109, (1988), pp. 839, Abstract No. 242975h.
Chemical Abstracts, vol. 110, (1989), p. 892, Abstract No. 127400a.
Chemical Abstracts, vol. 111, (1989), p. 921, Abstract No. 208180b.
Derwent Abstracts, No. 91–187135/26 for EP 434345.
Derwent Abstracts, No. 91–187136/26 for EP 434346.
Derwent Abstracts, No. 91–283191/39 for EP 448191.
Derwent Abstracts, No. 91–304859/42 for EP 451824.
Derwent Abstracts, No. 91–319187/44 for EP 454078.
On Line Ref. From IFI Claims Database for US 5.049.667, dated Sep. 17, 1991.

*Primary Examiner*—John Kight
*Assistant Examiner*—Dameron Jones
*Attorney, Agent, or Firm*—Karen L. Kimble

[57] ABSTRACT

Bicyclopolyazamacrocyclophosphonic acid compounds are disclosed which may form inert complexes with Gd, Mn or Fe ions. The overall charge of the complex can be varied to alter the in vivo biolocalization. Such complexes can be covalently attached to an antibody, antibody fragment or other biologically active molecule to form conjugates. The complexes and conjugates are useful as contrast agents for diagnostic purposes.

11 Claims, No Drawings ns, and suggests among various other compounds the possible use of a pyridine macrocyclomethylenecarboxylic acid. U.S. Pat. No. 4,880,008 (a CIP of U.S. Pat. No. 4,899,755) discloses additional imaging data for liver tissue of rats, but without any additional complexes being shown. U.S. Pat. No. 4,980,148 disclose gadolinium complexes for MRI which are non-cyclic compounds. C. J. Broan et al., *J. Chem. Soc., Chem. Commun.*, 1739–1741 (1990) describe some bifunctional macrocyclic phosphinic acid compounds. C. J. Broan et al., *J. Chem. Soc., Chem. Commun.*, 1738–1739 (1990) describe compounds that are triazabicyclo compounds. I. K. Adzamli et al., *J. Med. Chem.* 32, 139–144 (1989) describes acyclic phosphonate derivatives of gadolinium complexes for NMR imaging.

BICYCLOPOLYAZAMACROCYCLOPHOSPHONIC ACID HALF ESTERS

CROSS REFERENCES TO RELATED APPLICATIONS

This is a continuation of application Ser. No. 08/058,101 filed May 6, 1993, now abandoned, which is a continuation-in-part application of U.S. application Ser. No. 805,551, filed Dec. 10, 1991 now abandoned.

FIELD OF THE INVENTION

This invention concerns ligands that are bicyclopolyazamacrocyclophosphonic acids, and complexes and conjugates thereof, for use as contrast agents in magnetic resonance imaging (MRI). Some ligands and complexes are also useful as oral care agents and as scale inhibiting agents in water treatment systems. To better understand this invention, a brief background on MRI is provided in the following section.

BACKGROUND OF THE INVENTION

MRI is a non-invasive diagnostic technique which produces well resolved cross-sectional images of soft tissue within an animal body, preferably a human body. This technique is based upon the property of certain atomic nuclei (e.g. water protons) which possess a magnetic moment [as defined by mathematical equations; see G. M. Barrow, *Physical Chemistry*, 3rd Ed., McGraw-Hill, NY (1973)] to align in an applied magnetic field. Once aligned, this equilibrium state can be perturbed by applying an external radio frequency (RF) pulse which causes the protons to be tilted out of alignment with the magnetic field. When the RF pulse is terminated, the nuclei return to their equilibrium state and the time required for this to occur is known as the relaxation time. The relaxation time consists of two parameters known as spin-lattice (T1) and spin-spin (T2) relaxation and it is these relaxation measurements which give information on the degree of molecular organization and interaction of protons with the surrounding environment.

Since the water content of living tissue is substantial and variations in content and environment exist among tissue types, diagnostic images of biological organisms are obtained which reflect proton density and relaxation times. The greater the differences in relaxation times (T1 and T2) of protons present in tissue being examined, the greater will be the contrast in the obtained image [*J. Magnetic Resonance* 33, 83–106 (1979)].

It is known that paramagnetic chelates possessing a symmetric electronic ground state can dramatically affect the T1 and T2 relaxation rates of juxtaposed water protons and that the effectiveness of the chelate in this regard is related, in part, to the number of unpaired electrons producing the magnetic moment [*Magnetic Resonance Annual*, 231–266, Raven Press, NY (1985)]. It has also been shown that when a paramagnetic chelate of this type is administered to a living animal, its effect on the T1 and T2 of various tissues can be directly observed in the magnetic resonance (MR) images with increased contrast being observed in the areas of chelate localization. It has therefore been proposed that stable, non-toxic paramagnetic chelates be administered to animals in order to increase the diagnostic information obtained by MRI [*Frontiers of Biol. Energetics* I, 752–759 (1978); *J. Nucl. Med.* 25, 506–513 (1984); *Proc. of NMR Imaging Symp.* (Oct. 26–27, 1980); F. A. Cotton et al., *Adv.Inorg. Chem.* 634–639 (1966)]. Paramagnetic metal chelates used in this manner are referred to as contrast enhancement agents or contrast agents.

There are a number of paramagnetic metal ions which can be considered when undertaking the design of an MRI contrast agent. In practice, however, the most useful paramagnetic metal ions are gadolinium ($Gd^{+3}$), iron ($Fe^{+3}$), manganese ($Mn^{+2}$) and ($Mn^{+3}$), and chromium ($Cr^{+3}$), because these ions exert the greatest effect on water protons by virtue of their large magnetic moments. In a non-complexed form (e.g. $GdCl_3$), these metal ions are toxic to an animal, thereby precluding their use in the simple salt form. Therefore, a fundamental role of the organic chelating agent (also referred to as a ligand) is to render the paramagnetic metal non-toxic to the animal while preserving its desirable influence on T1 and T2 relaxation rates of the surrounding water protons.

Art in the MRI field is quite extensive, such that the following summary, not intended to be exhaustive, is provided only as a review of this area and other compounds that are possibly similar in structure. U.S. Pat. No. 4,899,755 discloses a method of alternating the proton NMR relaxation times in the liver or bile duct of an animal using $Fe^{+3}$-ethylene-bis(2-hydroxyphenylglycine) complexes and its derivative At the present time, the only commercial contrast agents available in the U.S. are the complex of gadolinium with diethylenetriaminepentaacetic acid (DTPA-$Gd^{+3}$—MAGNEVIST™ by Shering) and a DO3A derivative [1,4,7-tris(carboxymethyl)-10-(2-hydroxypropyl)-1,4,7,10-tetraazacyclododecanato]gadolinium (PROHANCE™ by Squibb). MAGNEVIST™ and PROHANCE™ are each considered as a non-specific/perfusion agent since it freely distributes in extracellular fluid followed by efficient elimination through the renal system. MAGNEVIST™ has proven to be extremely valuable in the diagnosis of brain lesions since the accompanying breakdown of the blood/brain barrier allows perfusion of the contrast agent into the affected regions. In addition to MAGNEVIST™, Guerbet is commercially marketing a macrocyclic perfusion agent (DOTAREM™) which presently is only available in Europe. PROHANCE™ is shown to have fewer side effects than Magnevist™. A number of other potential contrast agents are in various stages of development.

SUMMARY OF THE INVENTION

Surprisingly, it has now been found that various bicyclopolyazamacrocyclophosphonic acid ligands can be contrast agents. Furthermore, these ligands may have their charge modified, i.e. by the structure of the ligand and metal selected, which can effect their ability to be more site specific. Specifically, the present invention is directed to novel ligands that are bicyclopolyazamacrocyclophosphonic acid compounds of the formula

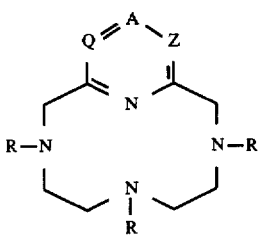

(I)

wherein:

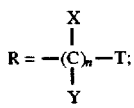

where:

X and Y are independently H, OH, $C_1$–$C_3$ alkyl or COOH;
n is an integer of 1, 2 or 3;
with the proviso that: when n is 2, then the sum of X and Y must equal two or more H; and when n is 3, then the sum of X and Y must equal three or more H;

T is H, $C_1$–$C_{18}$ alkyl, COOH, OH, $SO_3H$,

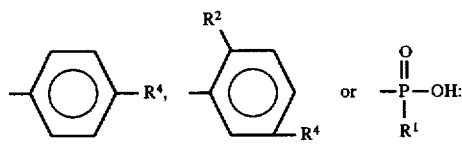

where:

$R^1$ is OH, $C_1$–$C_5$ alkyl or —O—($C_1$–$C_5$ alkyl);

$R^4$ is H, $NO_2$, $NH_2$, isothiocyanato, semicarbazido, thiosemicarbazido, maleimido, bromoacetamido or carboxyl;

$R^2$ is H or OH; with the proviso that when $R^2$ is OH, then the R term containing the $R^2$ must have all X and Y equal to H;

with the proviso that at least one T must be $P(O)R^1OH$, and with the proviso that when one T is

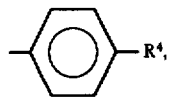

then one X or Y of that R term may be COOH and all other X and Y terms of that R term must be H;

A is CH, N, C—Br, C—Cl, C—$OR^3$, C—$OR^8$, $N^+$—$R^5$ $X^-$,

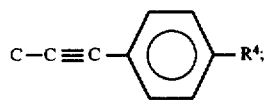

$R^3$ is H, $C_1$–$C_5$ alkyl, benzyl, or benzyl substituted with at least one $R^4$;

$R^4$ is defined as above;

$R^5$ is $C_1$–$C_6$ alkyl, benzyl, or benzyl substituted with at least one $R^4$;

$R^8$ is $C_1$–$C_{16}$ alkylamino;

$X^-$ is $Cl^-$, $Br^-$, $I^-$ or $H_3CCO_2^-$;

Q and Z independently are CH, N, $N^+$—$R^5$ $X^-$, C—$CH_2$—$OR^3$ or C—C(O)—$R^6$;

$R^5$ is defined as above;

$R^6$ is —O—($C_1$–$C_3$ alkyl), OH or $NHR^7$;

$R^7$ is $C_1$–$C_5$ alkyl or a biologically active material;

$X^-$ is defined as above; or pharmaceutically-acceptable salts thereof;

with the proviso that:

a) when Q, A or Z is N or $N^+$—$R^5$ $X^-$, then the other two groups must be CH;

b) when A is C—Br, C—Cl, C—$OR^3$ or C—$OR^8$, then both Q and Z must be CH;

c) the sum of the $R^4$, $R^7$ and $R^8$ terms, when present, may not exceed one; and d) only one of Q or Z can be C—C(O)—$R^6$ and when one of Q or Z is C—C(O)—$R^6$, then A must be CH.

When the above ligands of Formula (I) have at least two of the R terms T equal to $PO_3H_2$ [$P(O)R^1OH$ where $R^1$ is OH] and the third T equal H, COOH or $C_1$–$C_{18}$ alkyl; A, Q and Z are CH; n is 1; and X and Y independently are H or $C_1$–$C_3$ alkyl; then the ligands are useful for oral care. Particularly preferred are those ligands where in the three R terms T is $P(O)R^1OH$, where $R^1$ is OH; n is 1; and X and Y are H. The use of these ligands is discussed in our copending U.S. patent applications Ser. No. 805,600, filed Dec. 10, 1991, entitled "Oral Compositions for Inhibiting Calculus" by R. K. Frank, J. R. Garlich, J. Simon, G. E. Kiefer and D. A. Wilson (Attorney Docket No. C-38,337) and Ser. No. 805,598, filed Dec. 10, 1991, and entitled "Oral Compositions for Inhibiting Plaque Formation" by J. R. Garlich, R. K. Frank, J. Simon, G. E. Kiefer and D. A. Wilson (Attorney Docket No. C-39,198), the disclosures of which are hereby incorporated by reference.

When the above ligands of Formula (I) have:

in the R term at least two T equal $P(O)R^1OH$, where $R^1$ is OH, and in the other R term, T is COOH or $P(O)R^1OH$, and n, $R^1$, X, Y, A, Q and Z are defined as above;

in at least one R term T is $P(O)R^1OH$, where $R^1$ is OH, and in the other two R terms, T is COOH or $P(O)R^1OH$, and n, $R^1$, X, Y, A, Q and Z are defined as above; or in the R term three T equal $P(O)R^1OH$, where $R^1$ is $C_1$–$C_5$ alkyl or —O—($C_1$–$C_5$ alkyl), and n, $R^1$, X, Y, A, Q and Z are defined as above;

then the ligands are useful as contrast agents.

Particularly preferred are those ligands of Formula (I) where:

X and Y are H;

n is 1; or

A, Q and Z are CH.

Preferably the ligands and complexes of Formula (I) do not have all three T equal to $PO_3H_2$ [$P(O)R^1OH$ where $R^1$ is OH] when A, Q and Z are CH; although such complexes are useful as contrast agents or oral care agents.

Bifunctional ligands of Formula (I) are desirable to prepare the conjugates of this invention.

Such ligands must have:

one R term where the T moiety is

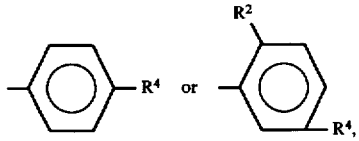

where $R^2$ and $R^4$ are defined as above, especially where in the two R terms not containing an $R^4$ term, both T terms are $P(O)R^1OH$, where $R^1$ is defined as above or where in the two R terms not containing an $R_4$ term, one T term is a COOH and the other T term is $P(O)R^1OH$, where $R^1$ is defined as above; preferably that moiety of the above T term where one of X or Y of that term is COOH; and also preferred are those ligands where n is 1 and/or the remaining X and Y terms are H; or A is $C-OR^3$ or $C-OR^8$, where $R^3$ and $R^8$ are defined as above or

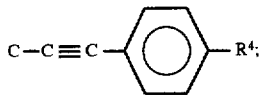

where $R^4$ is defined as above; or

A is CH, and one of Q or Z is CH and the other is $C-C(O)-R^6$, where $R^6$ is defined as above; especially those ligands where $R^6$ is $NHR^7$, where $R^7$ is a biologically active material.

The ligands of Formula (I) may be complexed with various metal ions, such as gadolinium ($Gd^{+3}$), iron ($Fe^{+3}$), and manganese ($Mn^{+2}$), with $Gd^{+3}$ being preferred. The complexes so formed can be used by themselves or can be attached, by being covalently bonded to a larger molecule such as a dextran, a polypeptide or a biologically active molecule, including an antibody or fragment thereof, and used for diagnostic purposes. Such conjugates and complexes are useful as contrast agents.

The complexes and conjugates of this invention can be designed to provide a specific overall charge which advantageously influences the invivo biolocalization and image contrast. For example, when the metal ion is +3 the following can be obtained:

(A) an overall charge of −2 or more—when in three R terms T is $P(O)R^1OH$, where $R^1$ is OH, and n is 1;

in two R terms T is $P(O)R^1OH$, where $R^1$ is OH, in the third R term T is COOH, and n is 1;

in two R terms T is $P(O)R^1OH$, where $R^1$ is OH, in the third R term T is $P(O)R^1OH$, where $R^1$ is $C_1-C_5$ alkyl, and n is 1; or in two R terms T is $P(O)R^1OH$, where $R^1$ is OH, in the third R term T is $P(O)R^1OH$, where $R^1$ is $-O-(C_1-C_5$ alkyl), and n is 1;

(B) an overall charge of −1—when in one R term T is $P(O)R^1OH$, where $R^1$ is OH, and in the other two R terms T is $P(O)R^1OH$, where $R^1$ is $-O-(C_1-C_5$ alkyl), and n is 1;

in one R term T is $P(O)R^1OH$, where $R^1$ is OH, and in the other two R terms T is $P(O)R^1OH$, where $R^1$ is $C_1-C_5$ alkyl, and n is 1; or in one R term T is $P(O)R^1OH$, where $R^1$ is OH, and in the other two R terms T is COOH, and n is 1;

(C) an overall neutral charge—when in the three R terms T is $P(O)R^1OH$, where $R^1$ is $-O-(C_1-C_5$ alkyl), and n is 1; or in the three R terms T is $P(O)R^1OH$, where $R^1$ is $C_1-C_5$ alkyl, and n is 1; or (D) an overall charge of +1—when one of A, Q or Z is $N^+-R^5$ $X^-$, where $R^5$ and $X^-$ are defined as above; and in one R term, the T moiety is $P(O)R^1OH$, where $R^1$ is $C_1-C_5$ alkyl or $-O-(C_1-C_5$ alkyl); and in the other two R terms, the T moiety is COOH or $P(O)R^1OH$, where $R^1$ is $C_1-C_5$ alkyl, $-O-(C_1-C_5$ alkyl); and all X and Y terms are H.

Both the complexes and conjugates may be formulated to be in a pharmaceutically acceptable form for administration to an animal.

Use of the ligands of this invention with other metal ions for diagnosis of disease states such as cancer is possible. The use of those complexes and conjugates is discussed in copending U.S. patent application Ser. No. 806,069, filed Dec. 10, 1991, entitled "Bicyclopolyazamacrocyclophosphonic Acid Complexes, and Conjugates Thereof, for Use as Radiopharmaceuticals" by G. E. Kiefer and J. Simon (Attorney Docket No. C-39,771), filed on even date herewith, the disclosure of which is hereby incorporated by reference.

DETAILED DESCRIPTION OF THE INVENTION

The compounds of Formula (I) are numbered for nomenclature purposes as follows:

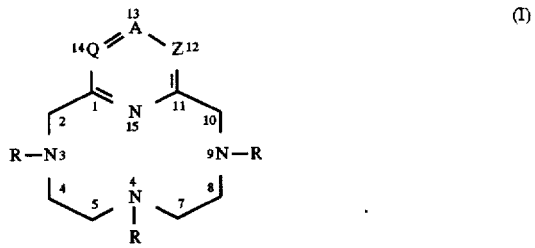

One aspect of the present invention concerns development of contrast agents having synthetic modifications to the paramagnetic chelate enabling site specific delivery of the contrast agent to a desired tissue. The advantage being increased contrast in the areas of interest based upon tissue affinity as opposed to contrast arising from non-specific perfusion which may or may not be apparent with an extracellular agent. The specificity of the ligand of Formula (I) may be controlled by adjusting the total charge and lipophilic character of the complex. The overall range of the charge of the complex is from −3 to +1. For example, for a complex having 2 or more $PO_3H_2$ groups, the overall charge is highly negative and bone uptake is expected; whereas when the overall charge of the complex is 0 (thus neutral), the complex may have the ability to cross the blood brain barrier and normal brain uptake may be possible.

Tissue specificity may also be realized by ionic or covalent attachment of the chelate to a naturally occurring or synthetic molecule having specificity for a desired target tissue. One possible application of this approach is through the use of chelate conjugated monoclonal antibodies which would transport the paramagnetic chelate to diseased tissue enabling visualization by $MR^1$. In addition, attachment of a paramagnetic chelate to a macromolecule can further increase the contrast agent efficiency resulting in improved contrast relative to the unbound chelate. Recent work by Lauffer (U.S. Pat. Nos. 4,880,008 and 4,899,755) has demonstrated that variations in lipophilicity can result in tissue-specific agents and that increased lipophilic character favors non-covalent interactions with blood proteins resulting in enhancement of relaxivity.

Additionally, the present contrast agents of Formula (I) which are neutral in charge are particularly preferred for forming the conjugates of this invention since undesirable ionic interactions between the chelate and protein are minimized which preserves the antibody immunoreactivity. Also the present neutral complexes reduce the osmolarity relative to $DTPA-Gd^{+3}$, which may alleviate the discomfort of injection.

While not wishing to be bound by theory, it is believed that when a charged complex of the invention is made (e.g.

possibly −2 or −3 for bone, −1 for liver, or +1 for heart), the variations in that chelate ionic charge can influence biolocalization. Thus, if the antibody or other directing moiety is also specific for the same site, then the conjugate displays two portions to aid in site specific delivery.

The terms used in Formula (I) and for this invention are further defined as follows. "$C_1$–$C_3$ alkyl", "$C_1$–$C_5$ alkyl", "$C_1$–$C_{18}$ alkyl", include both straight and branched chain alkyl groups. An "animal" includes a warmblooded mammal, preferably a human being.

"Biologically active material" refers to a dextran, peptide, or molecules that have specific affinity for a receptor, or preferably antibodies or antibody fragments.

"Antibody" refers to any polyclonal, monoclonal, chimeric antibody or heteroantibody, preferably a monoclonal antibody; "antibody fragment" includes Fab fragments and F(ab')$_2$ fragments, and any portion of an antibody having specificity toward a desired epitope or epitopes. When using the term "radioactive metal chelate/antibody conjugate" or "conjugate", the "antibody" is meant to include whole antibodies and/or antibody fragments, including semisynthetic or genetically engineered variants thereof. Possible antibodies are 1116-NS-19-9 (anti-colorectal carcinoma), 1116-NS-3d (anti-CEA), 703D4 (anti-human lung cancer), 704A1 (anti-human lung cancer), CC49 (anti-TAG-72), CC83 (anti-TAG-72) and B72.3. The hybridoma cell lines 1116-NS-19-9, 1116-NS-3d, 703D4, 704A1, CC49, CC83 and B72.3 are deposited with the American Type Culture Collection, having the accession numbers ATCC HB 8059, ATCC CRL 8019, ATCC HB 8301, ATCC HB 8302, ATCC HB 9459, ATCC HB 9453 and ATCC HB 8108, respectively.

As used herein, "complex" refers to a complex of the compound of the invention, e.g. Formula (I), complexed with a metal ion, where at least one metal atom is chelated or sequestered; "conjugate" refers to a metal ion chelate that is covalently attached to an antibody or antibody fragment. The terms "bifunctional coordinator", "bifunctional chelating agent" and "functionalized chelant" are used interchangeably and refer to compounds that have a chelant moiety capable of chelating a metal ion and a moiety covalently bonded to the chelant moiety that is capable of serving as a means to covalently attach to an antibody or antibody fragment.

The bifunctional chelating agents described herein (represented by Formula I) can be used to chelate or sequester the metal ions so as to form metal ion chelates (also referred to herein as "complexes"). The complexes, because of the presence of the functionalizing moiety (represented by $R^4$ or $R^8$ in Formula I), can be covalently attached to biologically active materials, such as dextran, molecules that have specific affinity for a receptor, or preferably covalently attached to antibodies or antibody fragments. Thus the complexes described herein may be covalently attached to an antibody or antibody fragment or have specific affinity for a receptor and are referred to herein as "conjugates".

As used herein, "pharmaceutically-acceptable salts" means any salt or mixtures of salts of a compound of Formula (I) which is sufficiently non-toxic to be useful in therapy or diagnosis of animals, preferably mammals. Thus, the salts are useful in accordance with this invention. Representative of those salts formed by standard reactions from both organic and inorganic sources include, for example, sulfuric, hydrochloric, phosphoric, acetic, succinic, citric, lactic, maleic, fumaric, palmitic, cholic, palmoic, mucic, glutamic, gluconic acid, d-camphoric, glutaric, glycolic, phthalic, tartaric, formic, lauric, steric, salicylic, methanesulfonic, benzenesulfonic, sorbic, picric, benzoic, cinnamic acids and other suitable acids. Also included are salts formed by standard reactions from both organic and inorganic sources such as ammonium or 1-deoxy-1-(methylamino)-D-glucitol, alkali metal ions, alkaline earth metal ions, and other similar ions. Particularly preferred are the salts of the compounds of Formula (I) where the salt is potassium, sodium, ammonium. Also included are mixtures of the above salts.

DETAILED DESCRIPTION OF THE PROCESS

The compounds of Formula (I) are prepared by various processes. Typical general synthetic approaches to such processes are provided by the reaction schemes given below.

In Scheme 1, the compounds of Forprea (I) are prepared wherein X and Y=H, n=1 (but would also apply if n=2 or 3 with the corresponding change in the reagent), T=PO$_3$H$_2$, and Q, A and Z=CH.

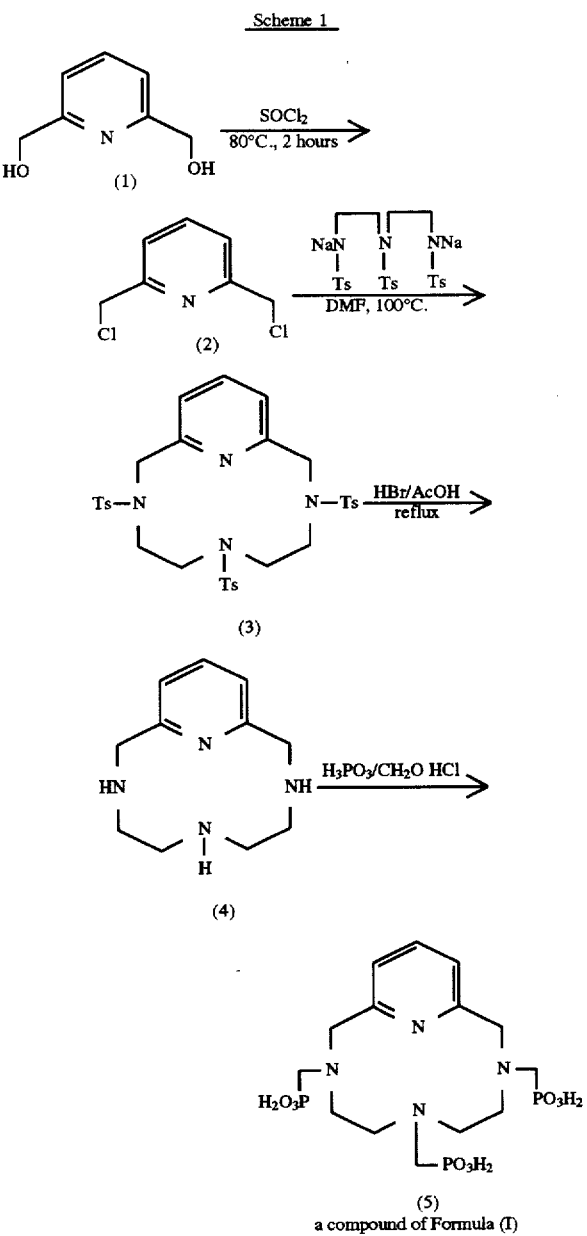

Scheme 2 prepares the compounds of Formula (I) wherein X and Y=H, n=1 (but would also apply if n=2 or 3 with the corresponding change in the reagent), T=

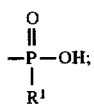

where $R^1$=—O—($C_1$-$C_5$ alkyl); and Q, A and Z=CH.

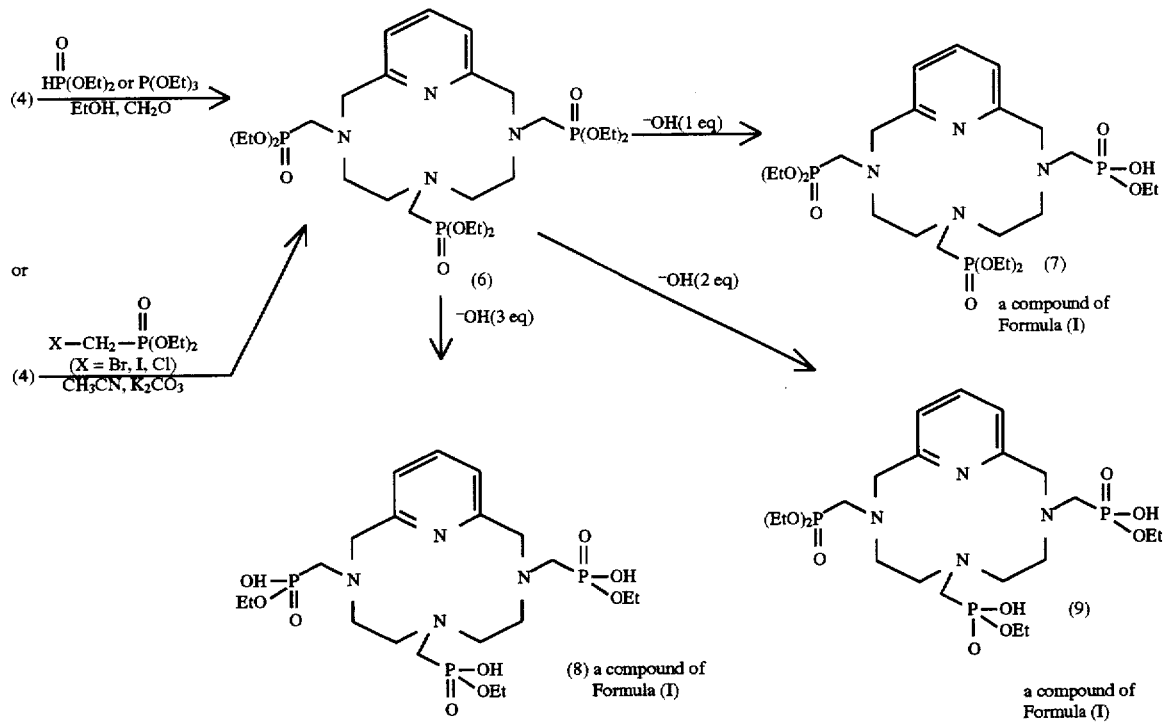

Scheme 3 prepares the compounds of Formula (I) wherein X and Y=H, n=1 (but would also apply if n=2 or 3 with the corresponding change in the reagent), T=

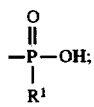

where $R^1$=$C_1$-$C_5$ alkyl; and Q, A and Z=CH.

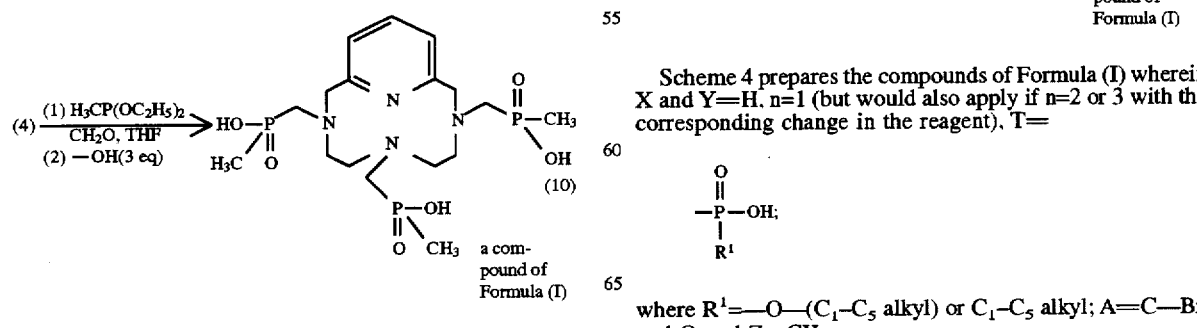

Scheme 4 prepares the compounds of Formula (I) wherein X and Y=H, n=1 (but would also apply if n=2 or 3 with the corresponding change in the reagent), T=

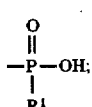

where $R^1$=—O—($C_1$-$C_5$ alkyl) or $C_1$-$C_5$ alkyl; A=C—Br, and Q and Z=CH.

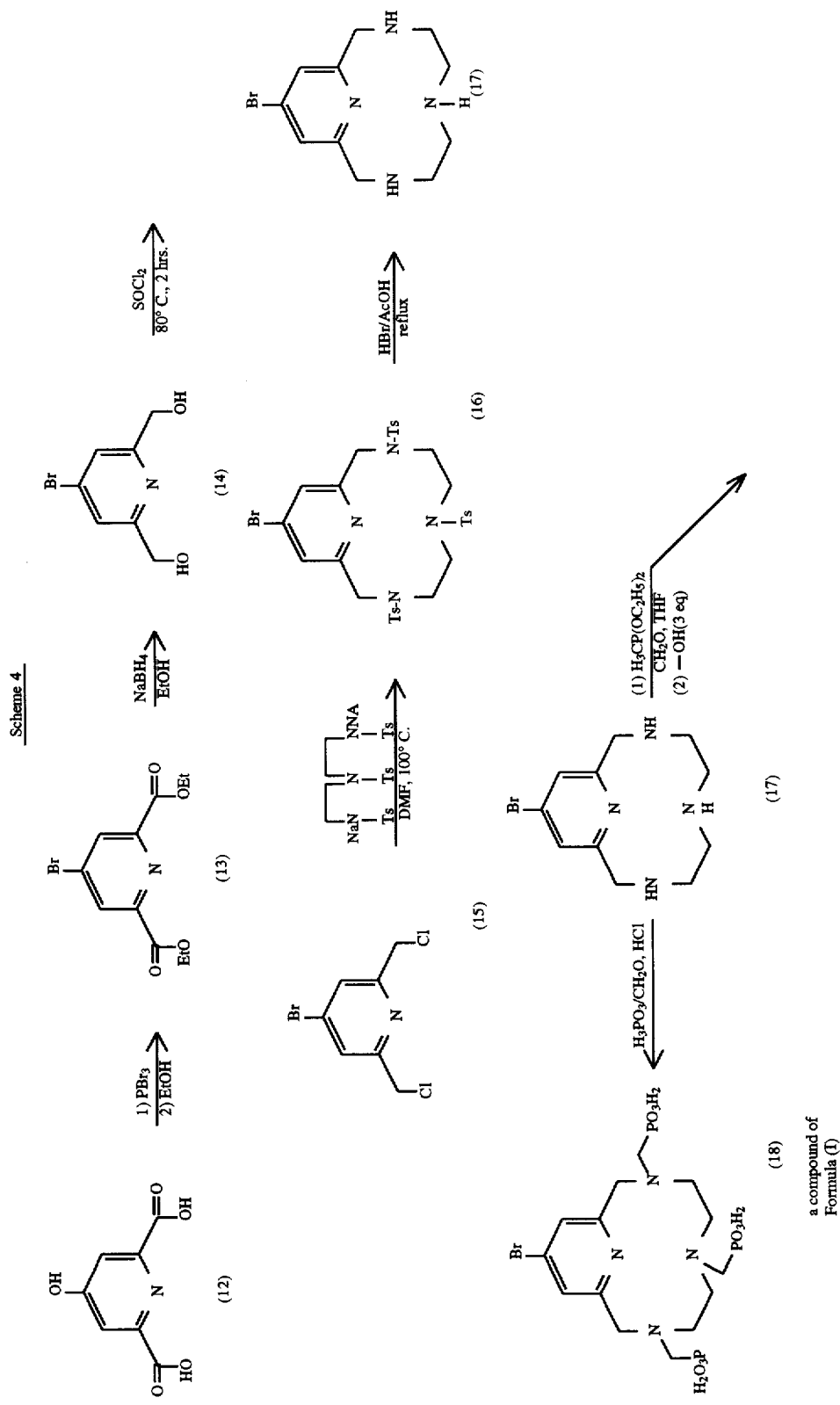

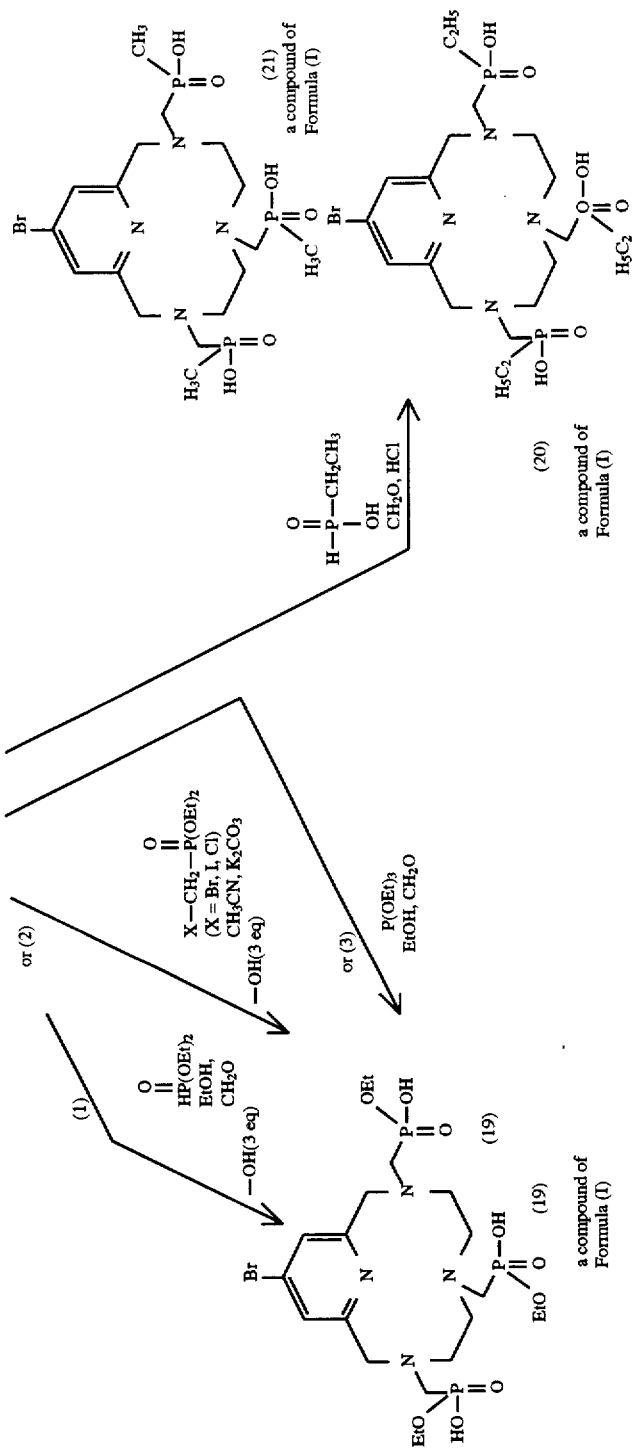

Scheme 5 prepares the compounds of Formula (I) wherein X and Y=H, n=1 (but would also apply if n=2 or 3 with the corresponding change in the reagent). T=
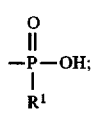
where $R^1$=—O—($C_1$-$C_5$ alkyl) or $C_1$-$C_5$ alkyl; A=
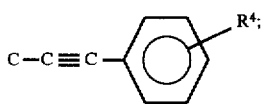
$R^4$=H, $NO_2$, $NH_2$ or SCN; and Q and Z=CH.
Scheme 5
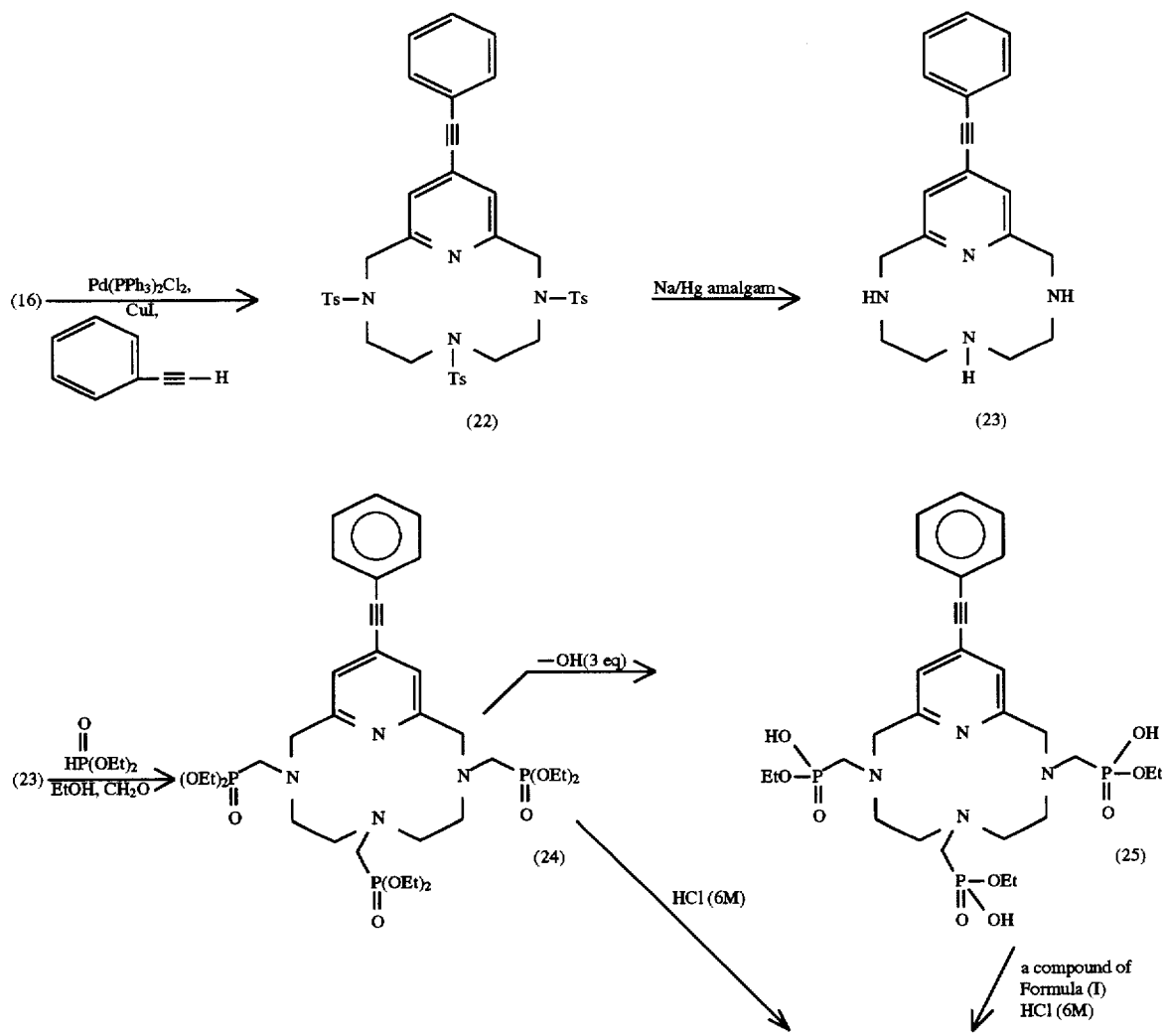

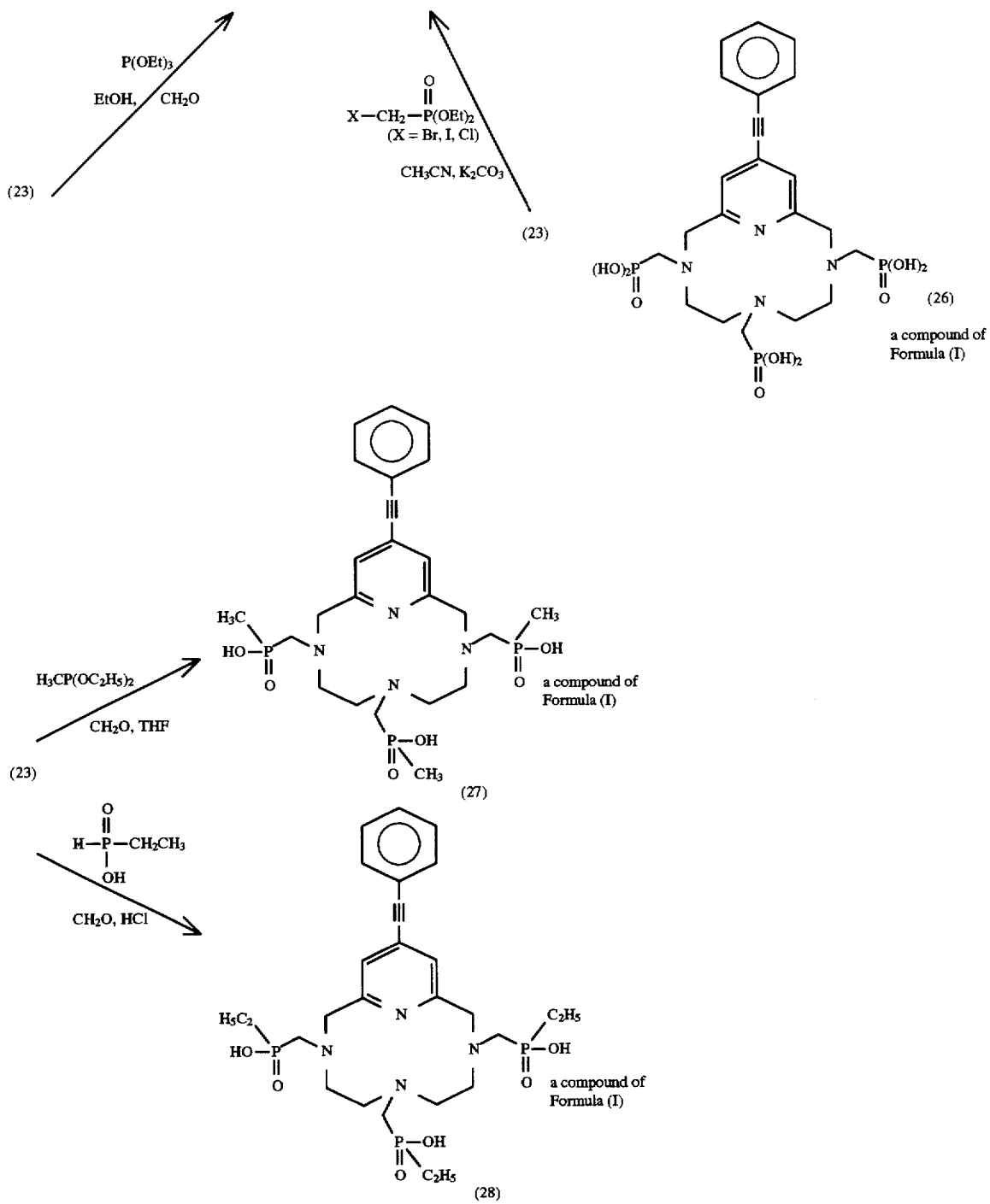
Scheme 6 prepares the compounds of Formula (I) wherein X and Y=H, n=1 (but would also apply if n=2 or 3 with the corresponding change in the reagent). T=
$$-\overset{\overset{O}{\|}}{\underset{R^1}{P}}-OH;$$
where $R^1$=—O—($C_1$-$C_5$ alkyl) or $C_1$-$C_5$ alkyl; A=C—$OR^8$, where $R^8$=$C_1$-$C_5$ alkylamino; and Q and Z=CH.

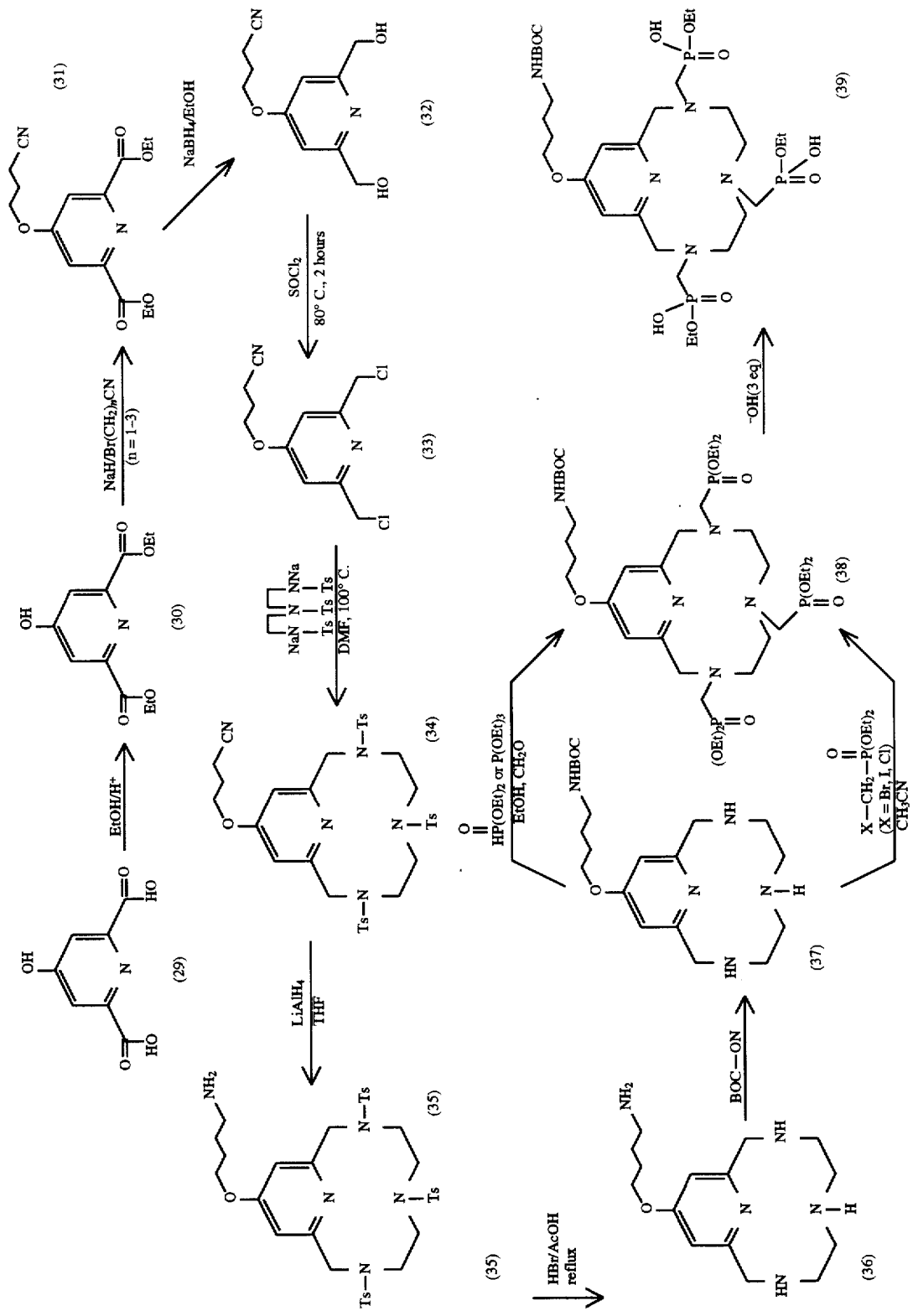

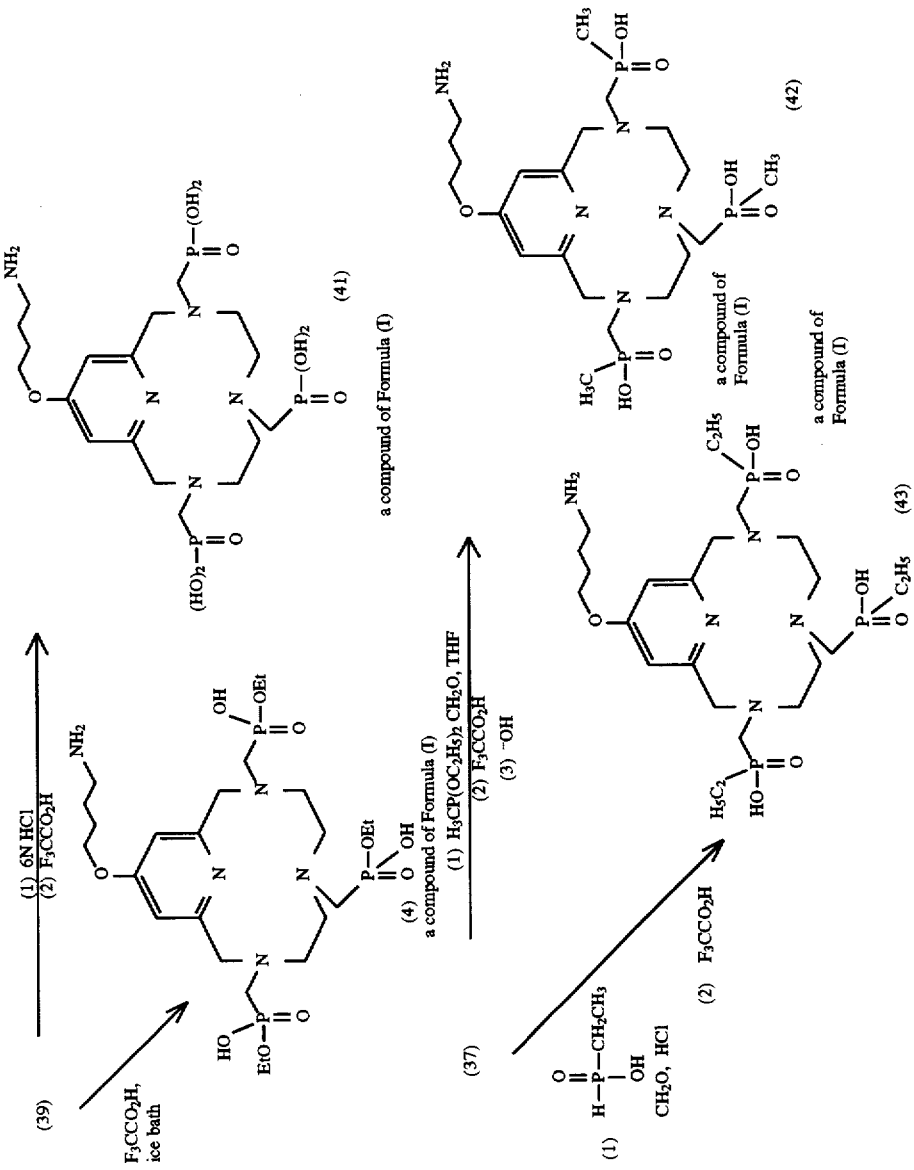

Scheme 7 prepares the compounds of Formula (I) wherein X and Y=H, n=1 (but would also apply if n=2 or 3 with the corresponding change in the reagent). T=
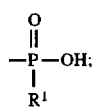
where $R^1$=—OH, —O—($C_1$-$C_5$ alkyl) or $C_1$-$C_5$ alkyl; Z=C—C(O)—$R^6$, where $R^6$=OH; and Q and A=CH.
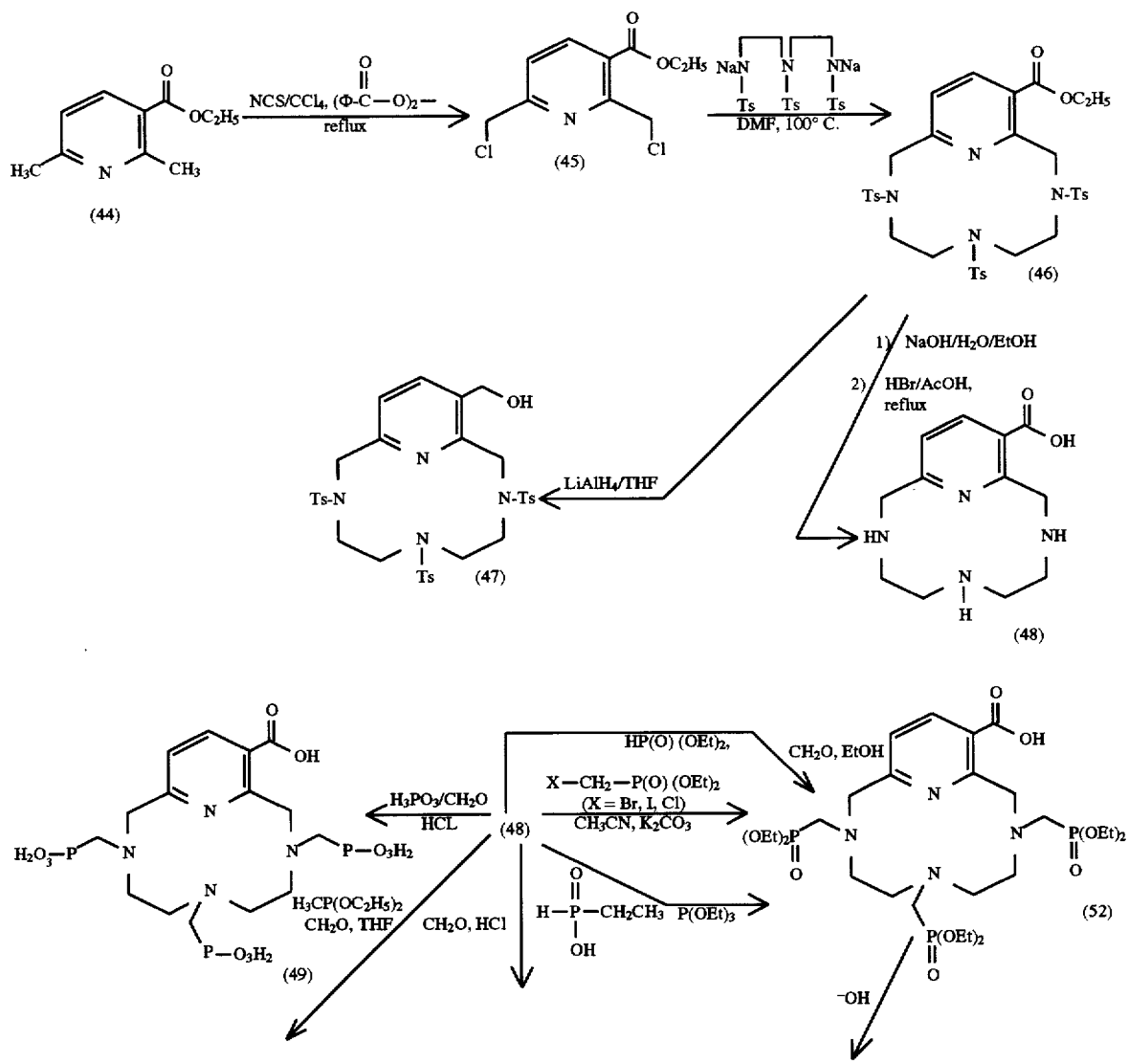

-continued
Scheme 7
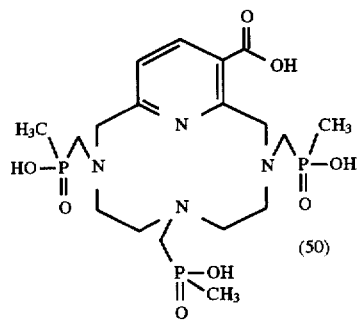
(50)
a compound of Formula (I)
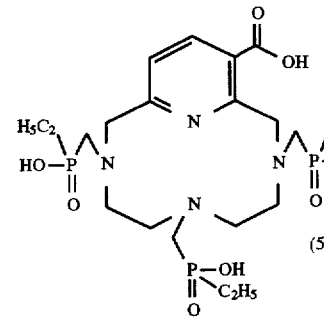
(51)
a compound of Formula (I)
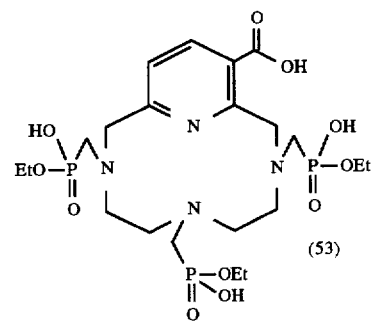
(53)
a compound of Formula (I)
Scheme 8 prepares the compounds of Formula (I) wherein X and Y=H, n=1 (but would also apply if n=2 or 3 with the corresponding change in the reagent). T=
where $R^1$=—OH, —O—($C_1$-$C_5$ alkyl) or $C_1$-$C_5$ alkyl; Z=C—$CH_2$—$OR^3$ where $R^3$=benzyl; and Q and A=CH.
Scheme 8
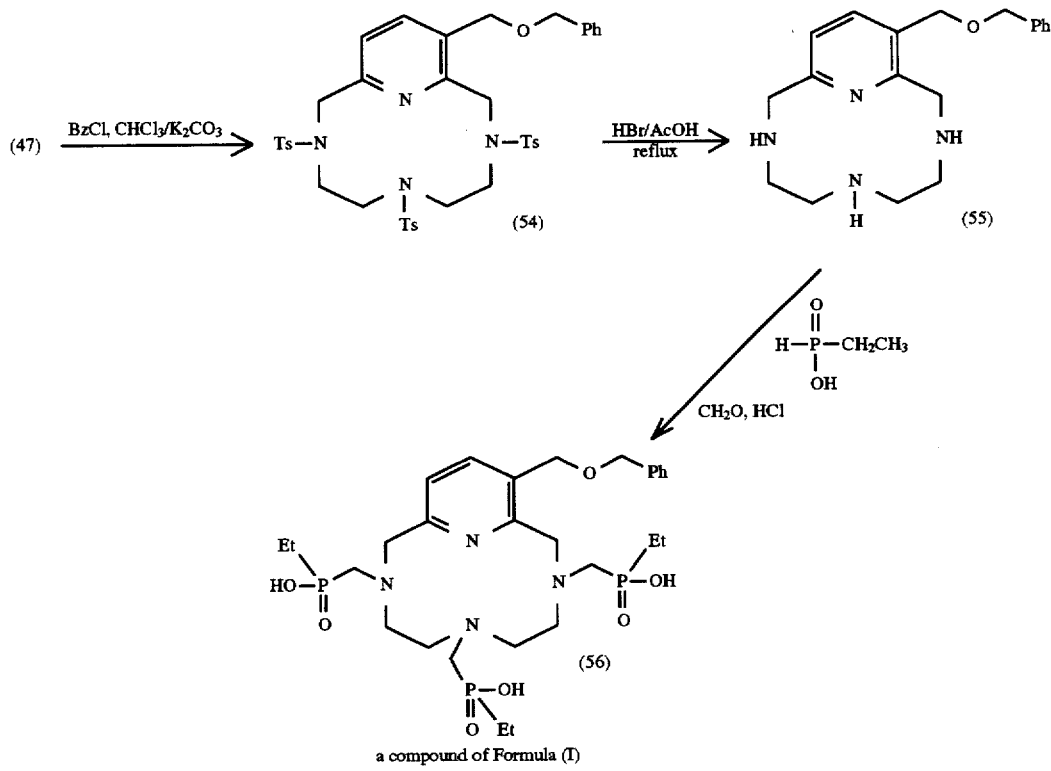

-continued
Scheme 8
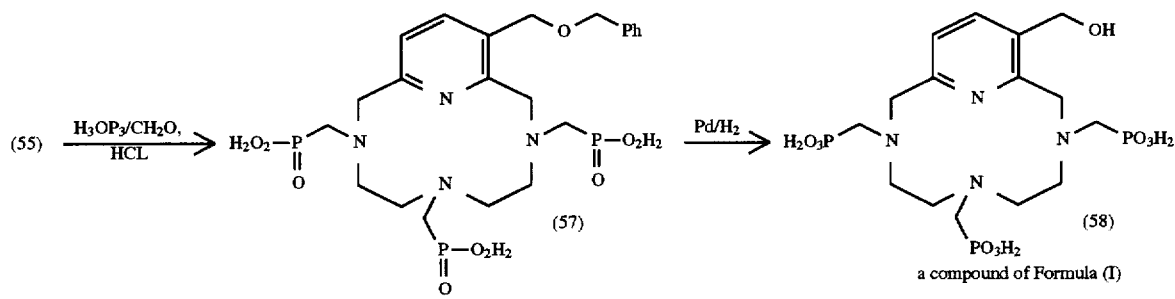
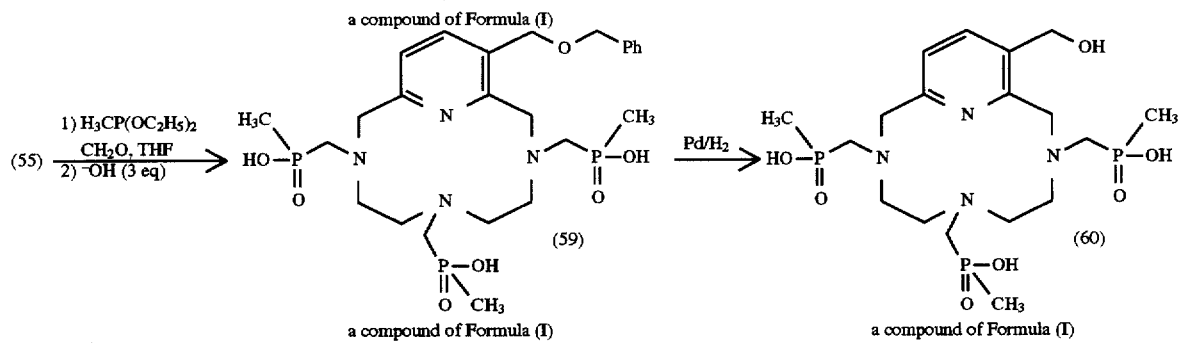
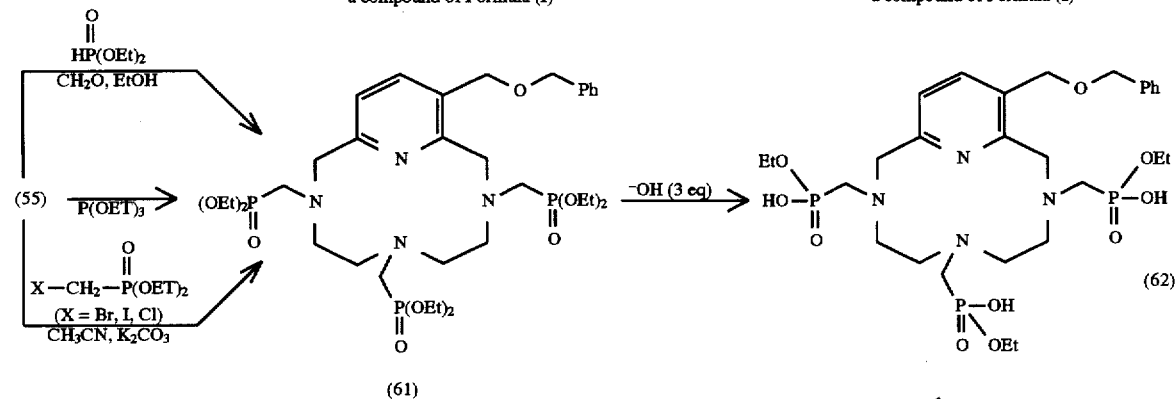
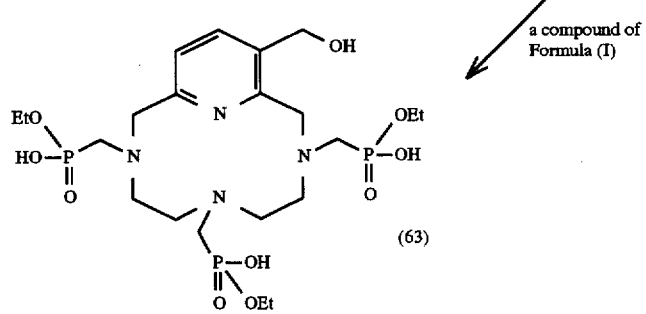
Scheme 9 prepares the compounds of Formula (I) wherein X and Y=H, n=1 (but would also apply if n=2 or 3 with the corresponding change in the reagent), T=
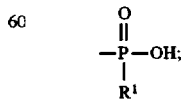
where $R^1$=—OH, —O—($C_1$-$C_5$ alkyl) or $C_1$-$C_5$ alkyl; A=N or N—$R^5$; $R^5$=$C_1$-$C_{16}$ alkyl halide; and Q and Z=CH.

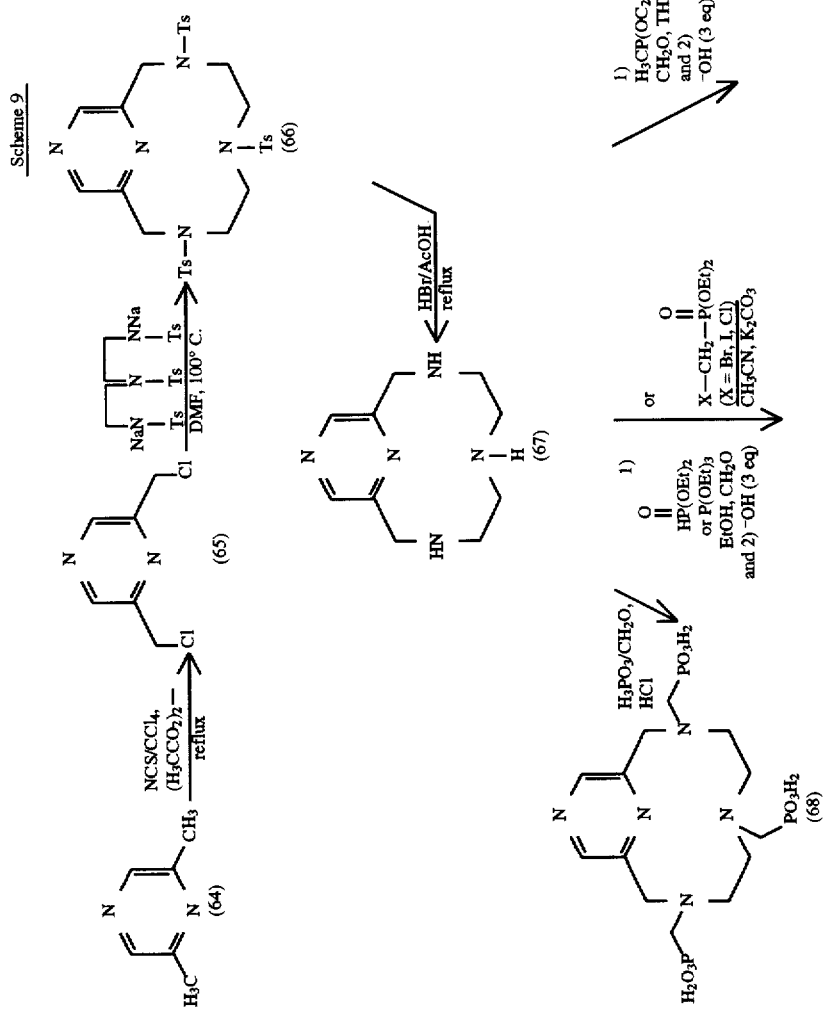

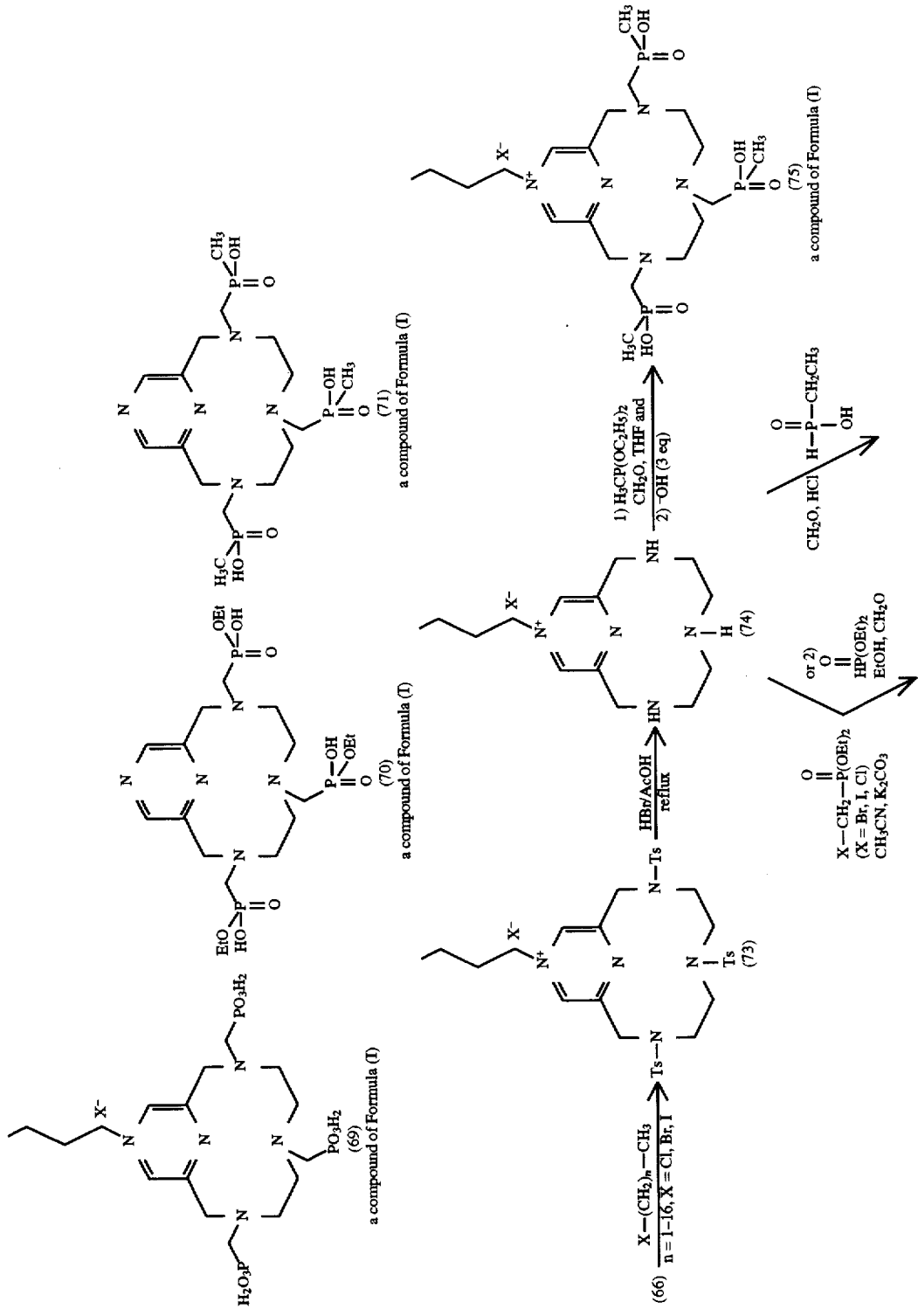

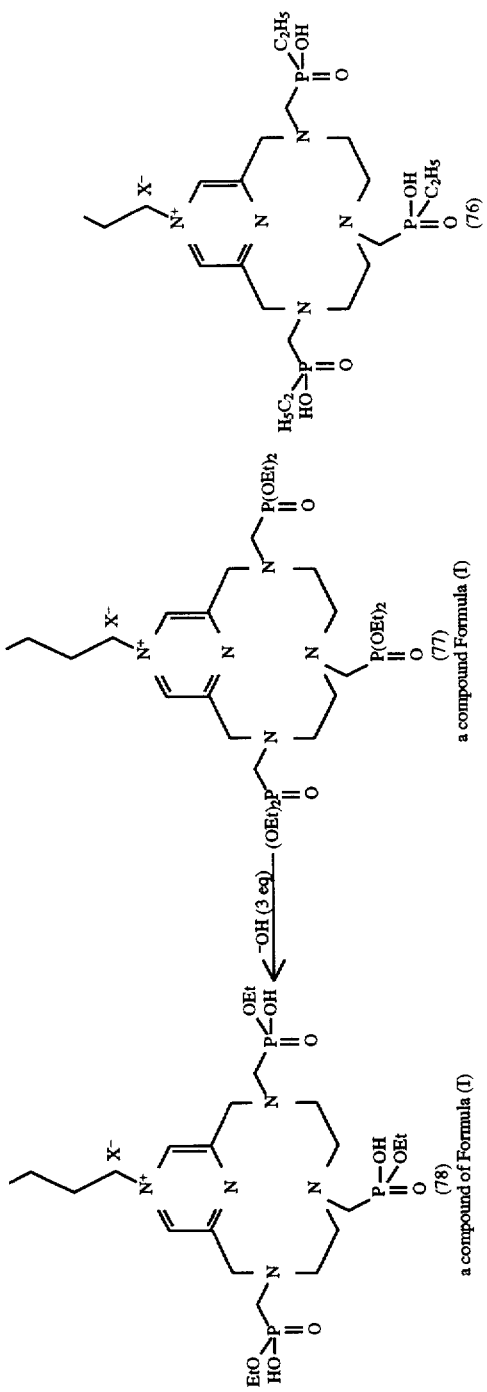

Scheme 10 prepares the compounds of Formula (I) wherein X and Y=H, n=1 (but would also apply if n=2 or 3 with the corresponding change in the reagent). T=

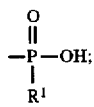

where $R^1$=—OH, —O—($C_1$-$C_5$ alkyl) or $C_1$-$C_5$ alkyl; Q=N—$R^5$; $R^5$=$C_1$-$C_{16}$ alkyl halide; and A and Z=CH.

Scheme 11 prepares the compounds of Formula (I) wherein X and Y=H, n=1 (but would also apply if n=2 or 3 with the corresponding change in the reagent). T=

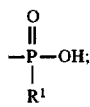

where $R^1$=—OH, —O—($C_1$-$C_5$ alkyl) or $C_1$-$C_5$ alkyl;

Scheme 10

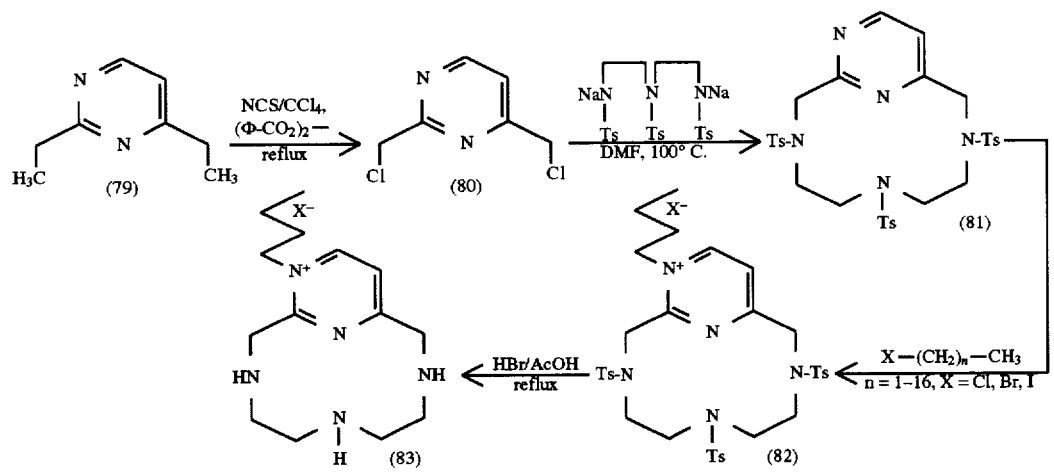

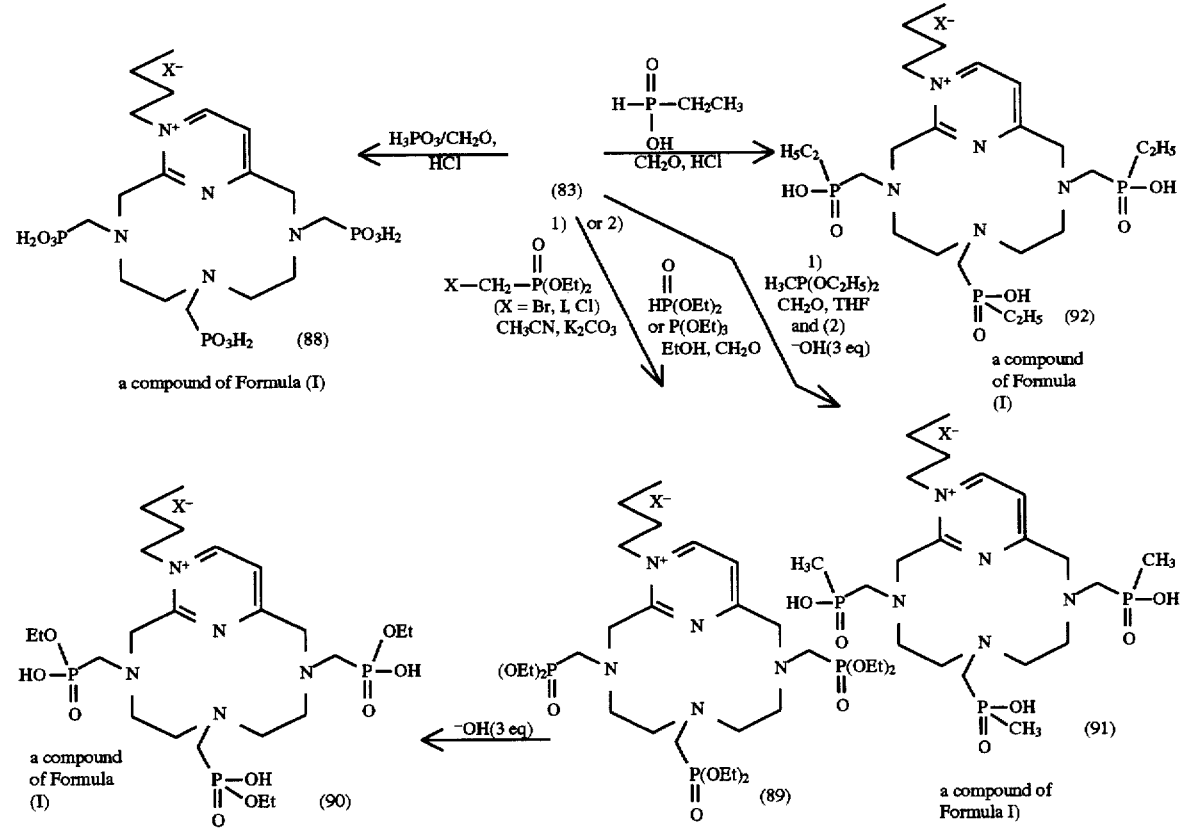

Q=N or N—R[5]. R[5]=$C_1$-$C_{16}$ alkyl halide; and A and Z=CH.
Alternate synthetic procedures allow selective introduction of the phosphonate at the N-6 position. This phospho-
Scheme 11
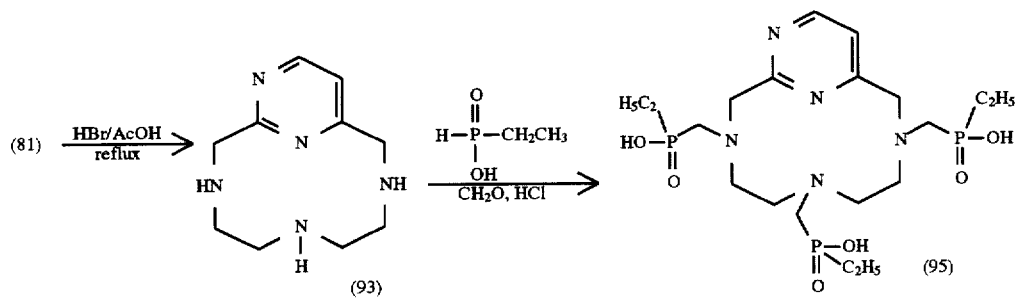
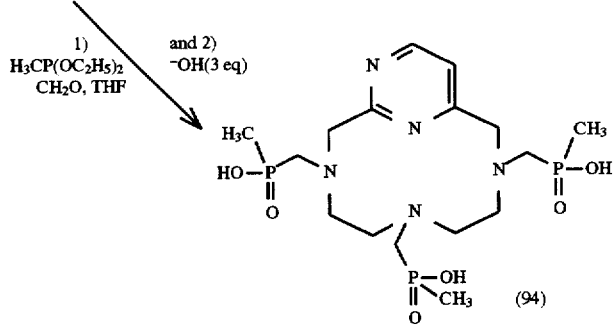
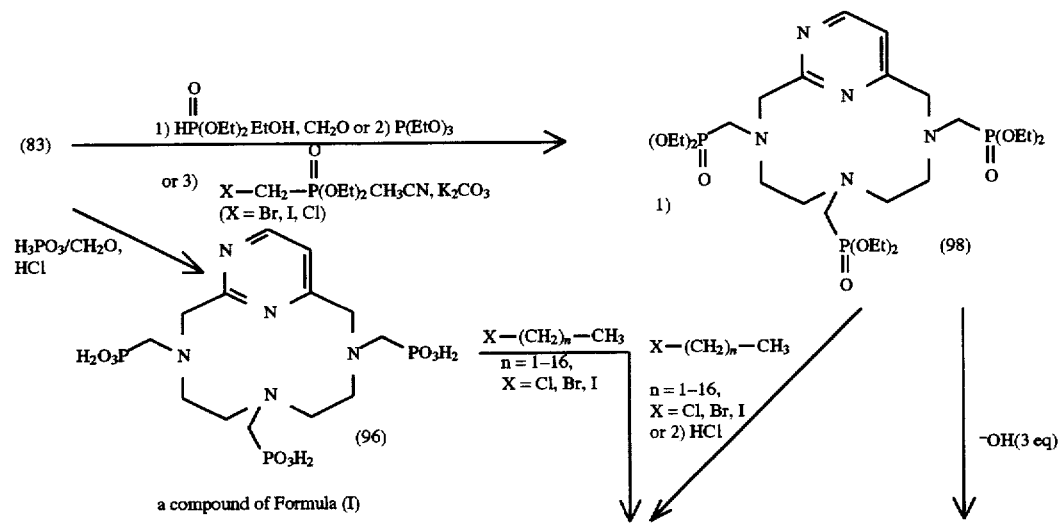
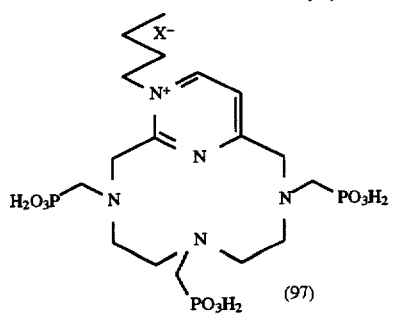
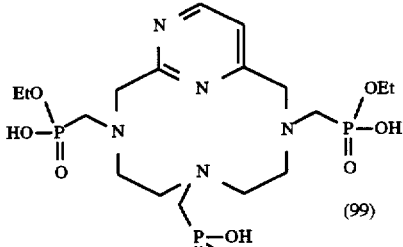

nate addition is accomplished by the reaction of (4) with formaldheyde sodium bisulfite addition to give quantitative conversion to the 4,9-substituted sulfonate derivative, which is then converted to the corresponding nitrile. Sebsequent phosphonomethylation and hydrolysis yields the desired product.

Scheme 12 prepares the compounds of Formula (I) therein X and Y=H, n=1 (but would also apply if n=2 or 3 with the corresponding change in the reagent). R at the 3 position has T=

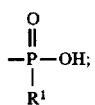

where $R^1$=—OH or —O—($C_1$–$C_5$ alkyl); and the other two R terms have T=COOH; and A, Q and Z=CH.

Scheme 12

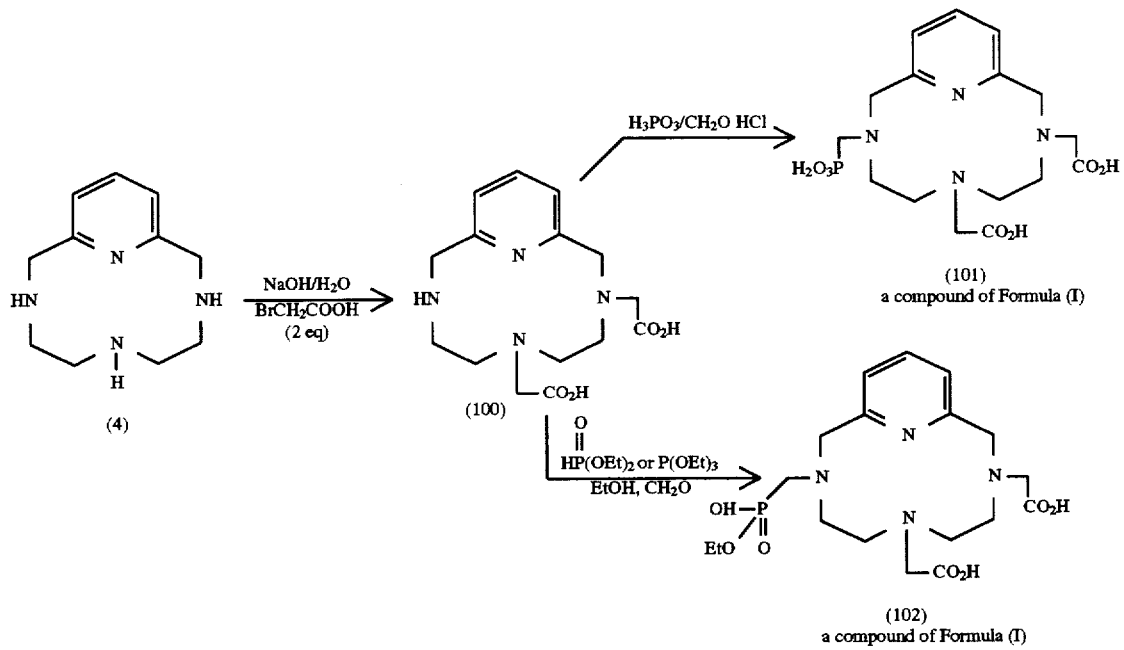

Scheme 13 prepares the compounds of Formula (I) wherein X and Y=H, n=1 (but would also apply if n=2 or 3 with the corresponding change in the reagent). R at the 3 and 6 positions have T=

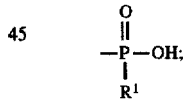

where $R^1$=OH or —O—($C_1$–$C_5$ alkyl); and the other R term at the 9 position has T=COOH; and A, Q and Z=CH.

Scheme 13

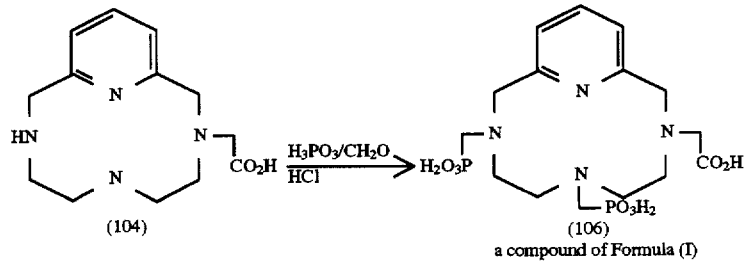

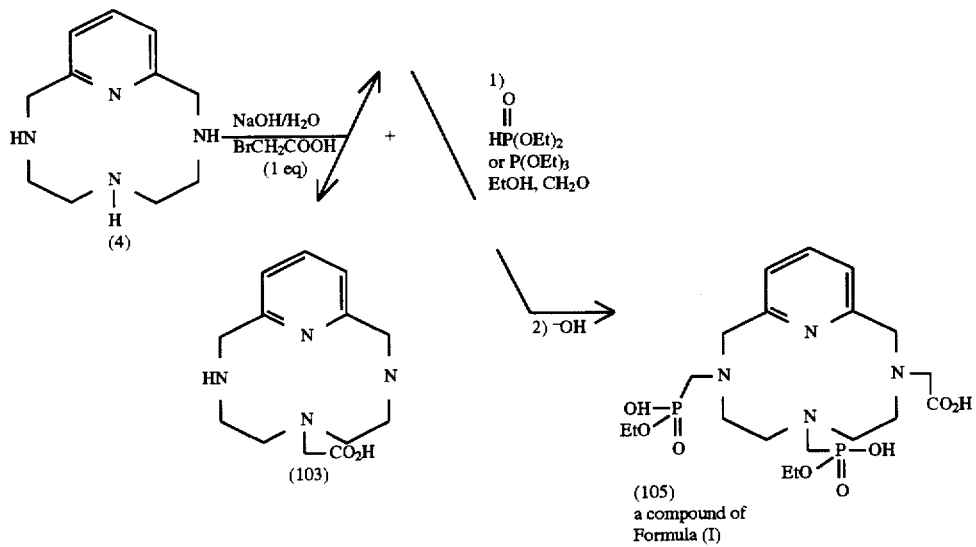
Scheme 14 prepares the compounds of Formula (I) wherein X and Y=H, n=1 (but would also apply if n=2 or 3 with the corresponding change in the reagent). R terms at the 3 and 9 positions have T=
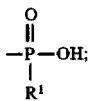
where $R^1$=—OH or —O—($C_1$–$C_5$ alkyl); and the other R term at the 6 position has T=COOH; and A, Q and Z=CH.
Scheme 14
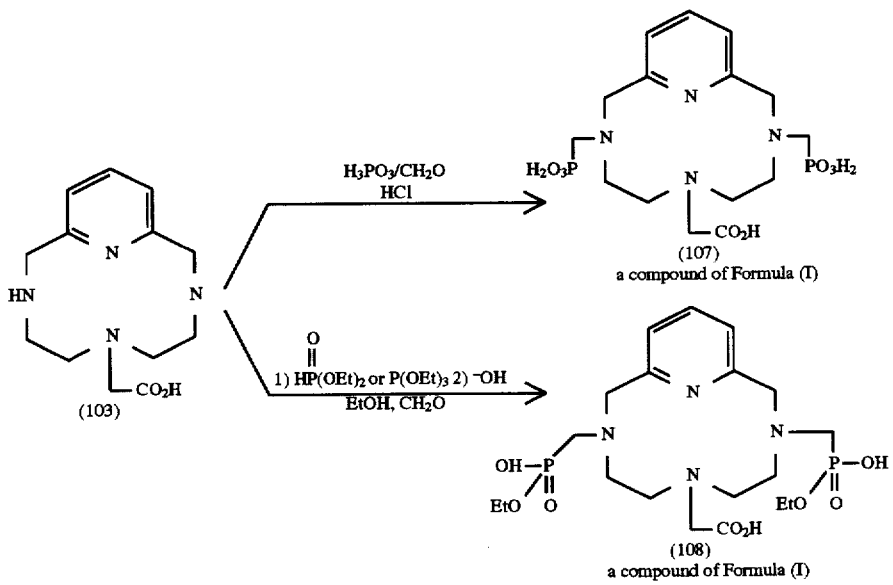

Scheme 15 prepares the compounds of Formula (I) wherein n=1 (but would also apply if n=2 or 3 with the corresponding change in the reagent). R terms at the 3 and 9 positions have T=

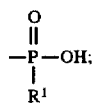

where $R^1$=—OH or —O—($C_1$-$C_5$ alkyl); and X and Y=H; the R term at the 6 position has T=

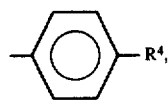

where $R^4$=$NO_2$ or $NH_2$; and one of X or Y=H and the other =COOH; and A, Q and Z=CH.

Scheme 15

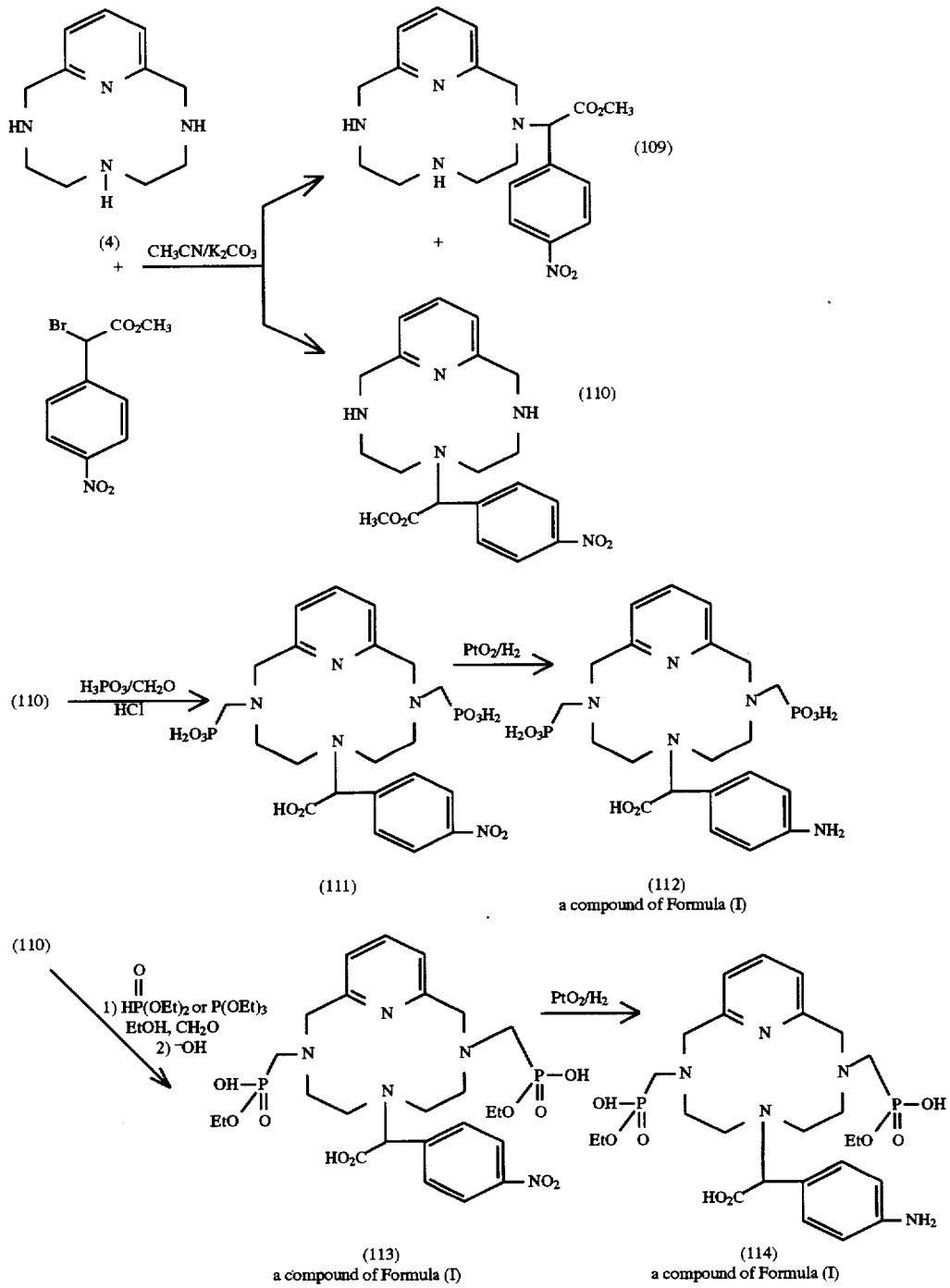

(109)

(110)

(111)

(112)
a compound of Formula (I)

(113)
a compound of Formula (I)

(114)
a compound of Formula (I)

Scheme 16 prepares the compounds of Formula (I) wherein n=1 (but would also apply if n=2 or 3 with the corresponding change in the reagent). R terms at the 3 and 6 positions have T=

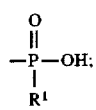

where $R^1$=—OH or —O—($C_1$-$C_5$ alkyl); and X and Y=H; the R term at the 9 position has T=

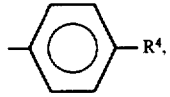

where $R^4$=$NO_2$ or $NH_2$; and one of X or Y=H and the other =COOH, A, Q and Z=CH.

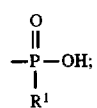

where $R^1$=—OH; and X and Y=H; the R term at the 3 and 9 positions have T=COOH; and A, Q and Z=CH.

Scheme 16

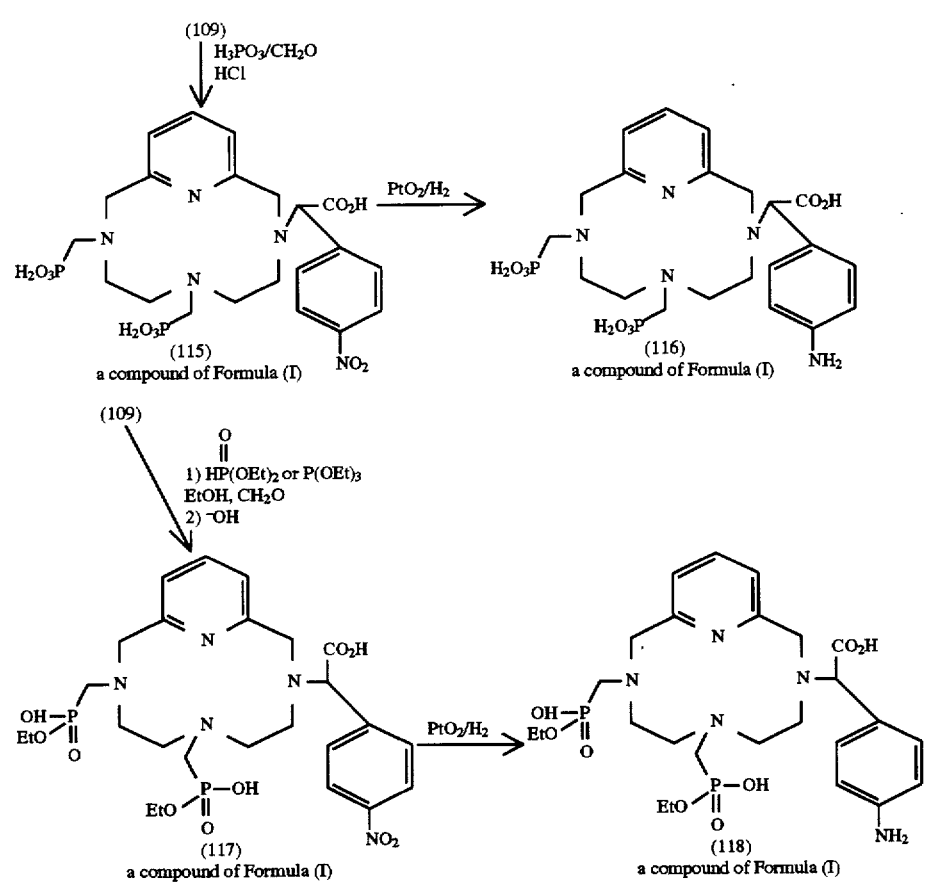

Scheme 17 prepares the compounds of Formula (I) wherein n=1 (but would also apply if n=2 or 3 with the corresponding change in the reagent), the R term at the 6 position has T=

Scheme 17

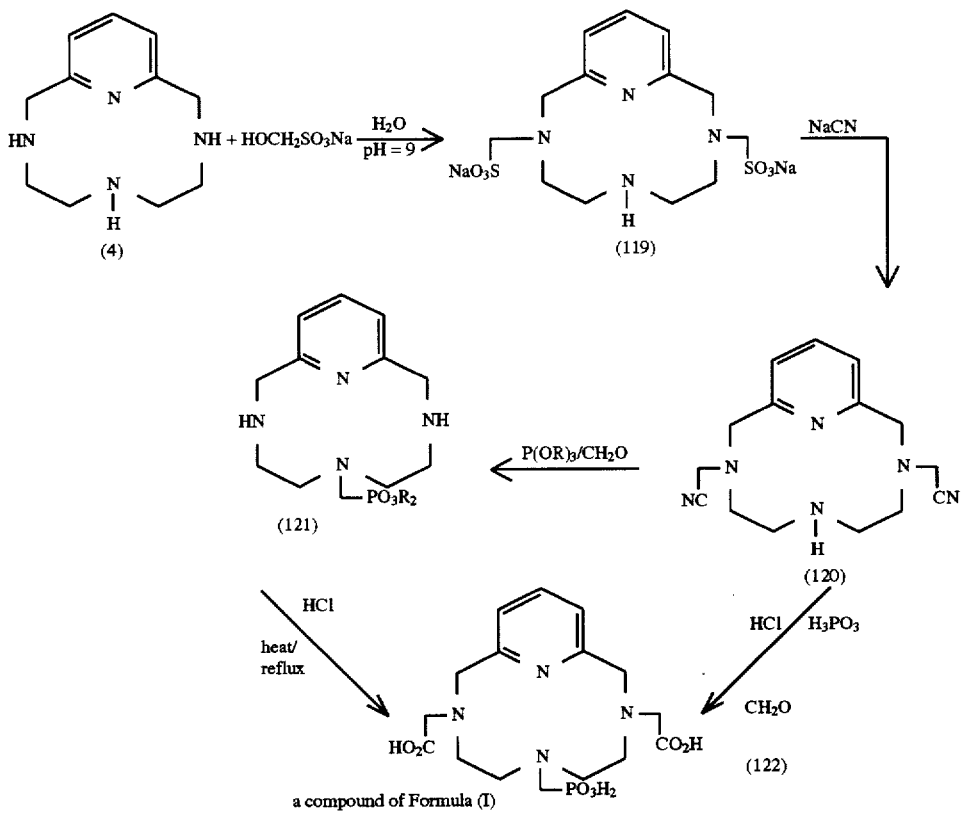

In the above Schemes, the general process discription illustrates specific steps that may be used to accomplish a desired reaction step. The general description of these process steps follows.

The synthetic Scheme 1 begins with a halogenation of commercially available bis-pyridyl alcohol (1) using thionyl chloride. Similar procedures for converting an alcohol to an electrophilic substrate, such as treatment with toluenesulfonyl chloride, HBr or HCl, should also result in a similarity reactive product which would work well in subsequent ring closure reactions. Macrocyclization procedures are numerous in the literature and the desired tetraazamacrocycle (3) was prepared according to the method of Stetter et al., *Tetrahedron* 37, 767–772 (1981). More general procedures have since been published which give good yields of similar macrocycles using milder conditions [A. D. Sherry et al., *J. Org. Chem.* 54, 2990–2992 (1989)]. Detosylation of the intermediate macrocycle [(3) to yield (4)] was accomplished under acidic conditions in good yield. Reductive detosylation procedures are also well known in the literature and can be adapted to the present reaction sequence. Phosphonomethylation to obtain the tris-aminophosphonic acid derative (5, PCTMP) was conducted under typical Mannich base conditions using phosphorous acid and formaldehyde.

In addition to phosphonic acid derivatives, phosphonate esters [e.g. of formula (6)] can also be prepared under organic conditions in alcohols or aprotic solvents (e.g. acetonitrile, benzene, toluene, tetrahydrofuran) and using the desired dialkylphosphite as the nucleophilic species (see Scheme 2). Depending upon the reactivity of the amine, these reactions may be conducted at a temperature between about −10° to about 100° C. In addition, trialkylphosphites can be employed under similar Mannich conditions to give the phosphonate ester via oxidation of phosphorous (III) to phosphorous (V) with simultaneous expulsion of one mole of alcohol (Arbuzov reaction). These reactions can be conducted with or without the presence of a solvent. When alcohols are employed as the solvent for either dialkyl or trialkyl phosphite reactions, it is beneficial to use the alcohol from which the corresponding phosphonate ester is derived in order to avoid alternative products arising from transesterification. Esters of this type are also prepared via N-alkylation of α-halo-dialkylphosphonates in solvents such as acetonitrile, chloroform, dimethylformamide, tetrahydrofuran or 1,4-dioxane with or without the addition of a non-nucleophilic base such as potassium carbonate at room temperature or above. The resulting perester intermediate is then readily hydrolyzed under basic conditions (aqueous hydroxide, pH=8–14°, 30°–110° C.) to give the corresponding half-acid derivative.

In Scheme 3, macrocyclic methylphosphinic acids (10 and 11) are prepared under conditions similar to those described in Scheme 2. Using diethoxymethylphosphine as the nucleophilic species and paraformaldehyde, condensation can be conducted in solvents such as tetrahydrofuran, dimethylformamide, dioxane, acetonitrile or alcholic media. The resulting phosphinate ester is then hydrolyzed under acid (6N HCl, 80°–100° C.) or basic (stoichiometric quantities of base, 40°–100° C.) conditions to give the corresponding methylphosphonic acid. Alternatively, the method devised by A. D. Sherry et al. (*Inorg. Chem.*, submitted 1991) using ethylphosphonic acid generated in situ can be used to obtain phosphinate derivatives having increased lipophilic character.

Scheme 4 illustrates an approach to incorporate additional functionality into the pyridine unit of the 12-membered tertaazamacrocycle. Thus, chelidamic acid (Sigma Chemical Company; 12) can be converted to the bis-halomethyl derivative (13) having appropriate substitution at the pyridyl 4-position. Transformations leading to this intermediate are general in nature and its preparation is described by Takalo et al. [*Acta Chemica Scandinavica* B 42, 373–377 (1988)]. Subsequent macrocyclization using this intermediate (15) can be accomplished by the standard DMF reaction at 100° C. with the sodiotritosylated triamine, or at room temperature with the tritosylated free base and potassium carbonate, sodium carbonate, or cesium carbonate as base to give products similar to those previously described. Subsequent reactions leading to phosphonate half-acids and phosphinate functionality are identical to those transformations and conditions described in the preceeding Schemes.

In Scheme 4, 4-halopyridyl substituted macrocycles (16) are described which can undergo substitution at the 4-position of the pyridyl moiety as described in Scheme 5. Thus, organometallic Pd(II) complexes can be employed to facilitate the coupling reaction between phenylacetylene and phenylacetylene derivatives and the pyridyl macrocycle. Typical reaction conditions for this transformation utilize anhydrous conditions with triethylamine as solvent and at reaction temperature between about 10° to about 30° C. for optimum yields. The identical product can also be obtained using Cu(I) phenylacetylide in anhydrous pyridine at a temperature between about 80° to about 1100° C. In addition, standard anionic alkylation procedures can be employed to affect substitution on the pyridine nucleus with, for example, sodioalkoxides in DMF or dioxane at from about 80° to about 1000° C. using bases such as potassium carbonate or sodium hydroxide. Macrocyclic tetraazamacrocycles (24, 25, 26, 27, 28) dervatized in this manner are compatible with transformations described in previous Schemes resulting in analogous phosphonate chelants.

A variation of 4-pyridyl substitution is described in Scheme 6 whereby the 4-hydroxypyridyl moiety (29) is alkylated with a bromoalkylnitrile yielding an intermediate ether linked nitrile (31) which is subsequently incorporated into the macrocyclic structure. This type of alkylation procedure is best accomplished under anhydrous conditions in an aprotic solvent such as tetrahydrofuran (THE) and using a non-nucleophilic base such as sodium hydride or butyllithium at temperatures between from about −30° to about 800° C. The generality of this approach has been described by Chaubet et al., for acyclic analogs [*Tetrahedron Letters* 31 (40), 5729–5732 (1990)]. The macrocyclic nitrile prepared in this manner can be reduced to the primary amine (36) by standard procedures followed by protection of the primary amine with 2-(t-butoxycarbonyloxyimino)-2-phenylacetonitrile (BOC-ON; 37). Subsequent functionalization of the macrocyclic secondary amines (38, 39, 40, 41, 42, 43) can then be accomplished by the procedures discussed with the additional requirement that the BOC protecting group be removed using trifluoroacetic acid as described in Scheme 6.

Functionalization can also be carried out on the 3-position of the pyridine ring within the macrocyclic structure as illustrated in Scheme 7. Newkome et al. [*Tetrahedron* 39(12), 2001–2008 (1983)] has previously described the synthesis of ethyl 2,6-halomethylnicotinate (45) which serves as the initial starting material in this synthetic route. Thus, the tris-tosylated macrocycle intermediate (46) can be detosylated under acidic conditions (HBr/AcOH, 25°–115° C.) with simultaneous hydrolysis to yield the nicotinic acid derivative (48), or reduction of the ester in refluxing ethanol prior to detosylation will result in the 3-hydroxymethyl intermediate (47). The nicotinic acid macrocycle can then be substituted into the general scheme for secondary amine functionalization to yield the various types of phosphonate chelants of Formula (I) (49, 50, 51, 52, 53).

In contrast, the 3-hydroxymethyl analog is advantageously protected prior to functionalization of the macrocyclic amines. The benzyl (Bz) protecting group is shown in Scheme 8 since it must be resistant to the severe acid conditions encountered in the detosylation step. After appropriate functionalization of the secondary amines has been accomplished as described in previous Schemes, the benzyl group is removed under mild catalytic hydrogenation conditions (58).

Macrocyclic derivatives can also be prepared as in Schemes 12–14 where both carboxylate and phosphonate chelating fuctionalities are present in the same molecule. Thus, varying degrees of carboxylate fuctionality can be introduced under typical aqueous alkylation procedures using bromoacetic acid. Following this step, the remaining amines can be phosphonomethylated by procedures discussed in previous Schemes using formaldehyde and phosphorous acid, dialkyl phosphonates or trialkyl phosphites.

Schemes 15 and 16 delineate a synthetic approach which introduces an aromatic nitrobenzyl substitutent at one of the macrocyclic nitrogen positions. Typically, the macrocyclic amine is mono-N-functionalized in an organic solvent such as acetonitrile or DMF at room temperature using a non-nucleophilic base such as potassium carbonate. Additional functionalization of the remaining nitrogen positions is then performed by methods and conditions described in previous Schemes. After the introduction of the desired chelating moieties, the nitro group is reduced using platinum oxide and hydrogen in water. In this form, the chelating agent is compatible with conjugation techniques which will enable attachment to larger synthetic or natural molecules.

Scheme 17 illustrates the synthesis of the macrocyclic compounds (4) where the amines at positions 3 and 9 are reacted with at least two moles of the sodium salt of hydroxymethanesulfonic acid in water at a pH of about 9 to provide the corresponding macrocyclic compound where positions 3 and 9 are the sodium salt of methanesulfonic acid (119). The sulfonic acid group is then displaced using sodium cyanide to form the corresponding cyanomethane derivative (120). The cyano group is hydrolyzed to the carboxylic acid either: simultaneously with the addition of phosphorous acid and formaldehyde; or by sequential reaction with a derivative of phosphorous acid and formaldehyde to form the phosphonic acid at the 6 position (121), followed by acid hydrolysis, at an elevated temperature, of the cyanato groups and any derivative moiety of the phosphorous acid present. The resulting compound is a macrocycle with two carboxylic acid groups at positions 3 and 9 and a phosphonic acid group at position 6. The phosphonomethylation can also be preformed by the methods discussed above.

The metal ions used to form the complexes of this invention are $Gd^{+3}$, $Mn^{+2}$, $Fe^{+3}$ and available commercially, e.g. from Aldrich Chemical Company. The anion present is halide, preferrably chloride, or salt free (metal oxide).

A "paramagnetic nuclide" of this invention means a metal ion which displays spin angular momentum and/or orbital angular momentum. The two types of momentum combine to give the observed paramagnetic moment in a manner that depends largely on the atoms bearing the unpaired electron and, to a lesser extent, upon the environment of such atoms.

The paramagnetic nuclides found to be useful in the practice of the invention are gadolinium ($Gd^{+3}$), iron ($Fe^{+3}$) and manganese ($Mn^{+2}$), with $Gd^{+3}$ being preferred.

The complexes are prepared by methods well known in the art. Thus, for example, see Chelating Agents and Metal Chelates, Dwyer & Mellor, Academic Press (1964), Chapter 7. See also methods for making amino acids in *Synthetic Production and Utilization of Amino Acids*, (edited by Kameko, et al.) John Wiley & Sons (1974). An example of the preparation of a complex involves reacting a bicyclopolyazamacrocyclophosphonic acid with the metal ion under aqueous conditions at a pH from 5 to 7. The complex formed is by a chemical bond and results in a stable paramagnetic nuclide composition, e.g. stable to the disassociation of the paramagnetic nuclide from the ligand.

The complexes of the present invention are administered at a ligand to metal molar ratio of at least about 1:1, preferably from 1:1 to 3:1, more preferably from 1:1 to 1.5:1. A large excess of ligand is undesirable since uncomplexed ligand may be toxic to the animal or may result in cardiac arrest or hypocalcemic convulsions.

The antibodies or antibody fragments which may be used in the conjugates described herein can be prepared by techniques well known in the art. Highly specific monoclonal antibodies can be produced by hybridization techniques well known in the art, see for example, Kohler and Milstein [*Nature*, 256, 495–497 (1975); and *Eur. J. Immunol.*, 6, 511–519 (1976)]. Such antibodies normally have a highly specific reactivity. In the antibody targeted conjugates, antibodies directed against any desired antigen or hapten may be used. Preferably the antibodies which are used in the conjugates are monoclonal antibodies, or fragments thereof having high specificity for a desired epitope (s). Antibodies used in the present invention may be directed against, for example, tumors, bacteria, fungi, viruses, parasites, mycoplasma, differentiation and other cell membrane antigens, pathogen surface antigens, toxins, enzymes, allergens, drugs and any biologically active molecules. Some examples of antibodies or antibody fragments are 1116-NS-19–9, 1116-NS-3d, 703D4, 704A1, CC49, CC83 and B72.3. All of these antibodies have been deposited in ATCC. A more complete list of antigens can be found in U.S. Pat. No. 4,193,983, which is incorporated herein by reference. The conjugates of the present invention are particularly preferred for the diagnosis of various cancers.

This invention is used with a physiologically acceptable carrier, excipient or vehicle therefore. The methods for preparing such formulations are well known. The formulations may be in the form of a suspension, injectable solution or other suitable formulations. Physiologically acceptable suspending media, with or without adjuvants, may be used.

An "effective amount" of the formulation is used for diagnosis. The dose will vary depending on the disease and physical parameters of the animal, such as weight. In vivo diagnostics are also contemplated using formulations of this invention.

Other uses of some of the chelants of the present invention may include the removal of undesirable metals (i.e. iron) from the body, attachment to polymeric supports for various purposes, e.g. as diagnostic agents, and removal of metal ions by selective extraction. The ligands of Formula (I) having in at least two R terms T equal to $P(O)R^1OH$ may be used for metal ion control as scale inhibitors. Some of these ligands can be used in less than stoichiometric amounts. Similar uses are known for compounds described in U.S. Pat. Nos. 2,609,390; 3,331,773; 3,336,221; and 3,434,969.

The invention will be further clarified by a consideration of the following examples, which are intended to be purely exemplary of the present invention.

Some terms used in the following examples are defined as follows:

LC=liquid chromatrography, purifications were carried out at low pressure using Dionex 2010i system fitted with a hand-packed Q-Sepharose™ anion exchange column (23×2 cm).

DMF=dimethylforamide.

AcOH=acetic acid.

ICP=inductively coupled plasma.

g=gram(s).

mg=milligrams.

kg=kilogram(s).

mL=milliliter(s).

μL=microliter(s).

pH Stability General Procedure

A stock $^{159}GdCl_3$ (or $^{153}SmCl_3$) solution was prepared by adding 2 μL of $3\times10^{-4}M$ $^{159}GdCl_3$ in 0.1N HCl to 2 mL of a $3\times10^{-4}M$ $GdCl_3$ carrier solution. Appropriate ligand solutions were then prepared in deionized water. The 1:1 ligand/ metal complexes were then prepared by combining the ligands (dissolved in 100–500 μL of deionized water) with 2 mL of the stock $^{159}GdCl_3$ solution, followed by through mixing to give an acidic solution (pH=2). The pH of the solution was then raised to 7.0 using 0.1N NaOH. The percent metal as a complex was then determined by passing a sample of the complex solution through a Sephadex™ G-50 column, eluting with 4:1 saline (85% $NaCl/NH_4OH$) and collecting 2×3 mL fractions. The amount of radioactivity in the combined elutions was then compared with that left on the resin (non-complexed metal is retained on the resin). The pH stability profile was generated by adjusting the pH of an aliquot of the complex solution using 1M NaOH or 1M HCl and determining the percent of the metal existing as a complex using the ion exchange method described above. The Sm results are known by experimental comparison to be identical for complexation and biodistribution of the ligands of this invention.

STARTING MATERIALS

EXAMPLE A

Preparation of 2,6-bis(chloromethyl)pyridine

To 100 mL of thionyl chloride that was cooled (ice bath) was added 24 g (0.17 mol) of 2,6-bis(hydroxymethyl) pyridine. After 30 min, the reaction mixture was warmed to room temperature, then refluxed for 1.5 hrs. After cooling the reaction mixture to room temperature, the solid which formed was filtered, washed with benzene and dried in vacuo. The solid was then neutralized with saturated $NaHCO_3$, filtered and dried to yield 23.1 g (71.5%) of the titled product as an off-white crystalline solid, mp 74.5°–75.5° C., and further characterized by:

$^1H$ NMR ($CDCl_3$) δ4.88 (s, 4H), 7.25–7.95 (m, 3H).

EXAMPLE B

Preparation of 3,6,9-tris(p-tolylsulfonyl)-3,6,9,15-tetraazabicyclo[9.3.1]pentadeca-1(15),11, 13-triene A DMF solution (92 mL) of 6.9 g (11.4 mmol) of 1,4,7-tris(p-tolylsulfonyl)diethylenetriamine disodium salt was stirred and heated to 100° C. under nitrogen. To the solution was added dropwise over 45 min 2 g (11.4 mmol) of 2,6-bis(chloromethyl)pyridine (prepared by the procedure of Example A) in 37 mL of DMF. When the addition was completed the reaction mixture was stirred at 40° C. for 12 hrs. To the reaction mixture was then added 50–75 mL of water, resulting in immediate dissolution of NaCl, followed by precipitation of the title product. The resulting slurry was then filtered and the solid washed with water and dried in vacuo. The title product was obtained as a light-tan powder, 6.5 g (86%), mp 168°–170° C. dec. and further characterized by:

$^1$H NMR (CDCl$_3$) δ2.40 (s, 3H), 2.44 (s, 6H), 2.75 (m, 4H), 3.30 (m, 4H), 4.28 (s, 4H), 7.27 (d, 2H), 7.34 (d, 4H), 7.43 (d, 2H), 7.65 (d, 4H), 7.75 (t, 1H); and $^{13}$C NMR δ21.48, 47.29, 50.37, 54.86, 124.19, 127.00, 127.11, 129.73, 135.04, 135.74, 138.95, 143.42, 143.73, 155.15.

EXAMPLE C

Preparation of 3,6,9,15-tetraazabicyclo[9.3.1] pentadeca-1(15),11,13-triene

A solution of HBr and AcOH was prepared by mixing 48% HBr and glacial ACOH in a 64:35 ratio. To 112 mL of the HBr/AcOH mixture was added 5.5 g (8.2 mmol) of 3,6,9-tris(p-tolylsulfonyl)-3,6,9,15-tetraazabicyclo[9.3.1] pentadeca-1(15),11,13-triene (prepared by the procedure of Example B) and the reaction mixture was heated at mild reflux with constant stirring for 72 hrs. The reaction mixture was then cooled to room temperature and concentrated to approximately 1/10 of the original volume. The remaining solution was stirred vigorously and 15–20 mL of diethyl ether was added. A off-white solid formed which was filtered, washed with diethyl ether, and dried in vacuo. The dry tetrahydrobromide salt was then dissolved in 10 mL of water, adjusted to pH 9.5 with NaOH (50% w/w) and continuously extracted with chloroform for 4 hrs. After drying over anhydrous sodium sulfate, the chloroform was evaporated to give a light-tan oil which gradually crystallized upon standing at room temperature to yield 1.2 g (71%) of the title product, mp 86°–88° C. and further characterized by:

$^1$H NMR (CDCl$_3$) δ2.21 (m, 4H), 2.59 (m, 4H), 3.06 (s, 3H), 3.85 (s, 4H), 6.89 (d, 2H), 7.44 (t, 1H); and $^{13}$C NMR δ48.73, 49.01, 53.63, 119.67, 136.29, 159.54.

EXAMPLE D

Preparation of 3,9-bis(sodium methylenesulfonate)- 3,6,9,15-tetraazabicyclo[9.3.1]pentadeca-1(15),11, 13-triene (PC2S)

An aqueous solution (10.0 mL) of 3,6,9,15-tetraazabicyclo[9.3.1]pentadeca-1(15),11,13-triene (prepared by the procedure of Example C), 1.03 g (5.0 mmol) was added with 0.5 mL of concentrated HCl and stirred for 10 min to ensure complete dissolution. The resulting solution had a pH of 8.6. To the solution was then added 1.37 g (10.2 mmol) of HOCH$_2$SO$_3$Na with 5 mL of deionized water. The solution was heated at 60° C. for 10 min and the pH dropped to 5.6. After cooling, the pH was adjusted to 9.0 with 1M aqueous sodium hydroxide, followed by lyophilization to give the desired product as a white solid in a quantative yield and characterized by:

$^1$H NMR (D$_2$O) δ2.87 (t, 4H), 3.18 (t, 4H), 3.85 (s, 4H), 4.11 (s, 4H), 7.03 (d, 2H), 7.55 (t, 1H); and $^{13}$C NMR (D$_2$O) δ48.52, 54.04, 58.92, 79.09, 123.90, 141.37, 161.89.

EXAMPLE E

Preparation of 3,9-bis(methylenenitrile)-3,6,9,15-tetraazabicyclo[9.3.1]pentadeca-1(15),11,13-triene To an aqueous solution, 10.0 mL, of 3,9-bis(sodium methylenesulfonate)-3,6,9,15-tetraazabicyclo[9.3.1] pentadeca-1(15),11,13-triene (prepared by the procedure of Example D), 2.26 g (5 mmol), was added 0.6 g (12.24 mmol) of sodium cyanide. The mixture was stirred for 3 hrs at room temperature. The pH of the reaction mixture was about 10. The pH was adjusted to above 13 with concentrated aqueous sodium hydroxide. The product precipitated and was extracted with chloroform (3×20 mL), dried over anhydrous magnesium sulfate, and filtered. Upon removal of solvent and concentration in vacuo, the desired product was isolated as a waxy, white powder, 1.0 g (71%) and characterized by:

$^1$H NMR (CDCl$_3$) δ2.03 (br s, 4H), 2.64 (m, 4H), 3.82 (s, 4H), 3.90 (s, 4H), 7.14 (d, 2H), 7.62 (t, 1H); and $^{13}$C NMR (CDCl$_3$) δ46.08, 46.64, 52.89, 60.78, 115.31, 122.02, 137.57, 157.33.

EXAMPLE F

Preparation of 3,9-bis(methylenenitrile)-6-(methylenedimethylphosphonate)-3,6,9,15-tetraazabicyclo[9.3.1]pentadeca-1(15),11,13-triene 3,9-bis(methylenenitrile)-3,6,9,15-tetraazabicyclo[9.3.1] pentadeca-1(15),11,13-triene (prepared by the procedure of Example E), 285 mg (1.0 mmol) was combined with 60 mg (2.0 mmol, excess) of paraformaldehyde and 0.354 mL (372 mg, 3.0 mmol, excess) of trimethylphosphite. The mixture was gently stirred for 10 min to obtain a slurry, then heated to 90° C. for 1 hr. After the excess reagents and byproducts were removed in vacuo (1 hr at 125° C./0.01 mmHg), he resulting dark brown residue was dissolved in 20 mL of chloroform and washed with deionized water (5×15 mL). The organic layer was dried over anhydrous magnesium sulfate, filtered, and the excess solvents evaporated in vacuo to give the desired product as a yellow waxy solid, 168 mg (41%) and characterized by:

$^1$H NMR (CDCl$_3$) δ2.61 (br s, 8H), 2.73 (d, 2H), 3.62 and 3.68 (s, 6H), 3.73 (s, 4H), 3.84 (s, 4H), 7.06 (d, 2H), 7.57 (t, 1H); and $^{13}$C NMR (CDCl$_3$) δ44.44, 50.74, 51.03, 51.85, 52.51, 60.28, 115.61, 122.27, 137.24, 156.61.

EXAMPLE G

Preparation of 3,6,9,15-tetraazabicyclo[9.3.1] pentadeca-1(15),11,13-triene-3,6,9-methylenediethylphosphonate A mixture of 1 g (4.8 mmol) of 3,6,9,15-tetraazabicyclo [9.3.1]pentadeca-1(15),11,13-triene (prepared by the procedure of Example C), 4.8 g (28.8 mmol) of triethyl phosphite and 864 mg (28.8 mmol) of paraformaldehyde was heated at 90° C. with constant stirring for 45 min. The reaction mixture was concentrated in vacuo and the viscous oil chromatographed on a basic alumina column, eluting with chloroform. After concentration of the organic eluent, the desired product was isolated as a colorless oil, 2.0 g (64%) and characterized by:

$^1$H NMR (CDCl$_3$) δ1.23 (m, 18H), 2.77 (m, 12H), 3.04 (d, 6H), 4.13 (m, 12H), 7.17 (d, 2H), 7.60 (t, 1H); and $^{13}$C NMR (CDCl$_3$) δ16.43, 50.03, 50.31, 50.43, 50.77, 51.23, 51.38, 52.63, 53.30, 60.86, 60.92, 61.63, 61.74, 61.83, 61.93, 62.32, 76.46, 76.97, 77.18, 77.48, 122.50, 137.10, 157.18; and $^{31}$P NMR (CDCl$_3$) δ24.92 (s, 2P), 24.97 (s,1P).

EXAMPLE H

Preparation of 3,6,9,15-tetraazabicyclo[9.3.1] pentadeca-1(15),11,13-triene-3,6,9-methylenedi(n-propyl)phosphonate To 3 mL of a chloroform/dioxane solution (1:1) was added 100 mg (0.48 mmol) of 3,6,9,15-tetraazabicyclo

[9.3.1]pentadeca-1(15),11,13-triene (prepared by the procedure of Example C), 318 mg (1.53 mmol) of tripropyl phosphite and 46 mg (1.53 mmol) of paraformaldehyde. The reaction mixture was heated at 90° C. with stirring for 1 hr. The resulting homogenous solution was concentrated in vacuo to give a viscous oil which was chromatographed on a neutral alumina column, eluting with chloroform. After concentration of the organic eluent, the desired product was isolated as a colorless oil, 320 mg (90%) and characterized by:

$^1$H NMR (CDCl$_3$) δ0.88 (m, 18H), 1.61 (m, 12H), 2.72 (m, 12H), 3.03 (d, 6H), 3.97 (m, 12H), 7.13 (d, 2H), 7.55 (t, 1H); and $^{13}$C NMR (CDCl$_3$) δ9.96, 23.73, 49.84, 50.14, 50.26, 50.57, 51.11, 51.23, 52.43, 53.01, 60.78, 60.84, 67.27, 67.40, 122.48, 137.04, 157.16; and $^{31}$P NMR (CDCl$_3$) δ24.98 (3P).

EXAMPLE I

Preparation of 3,6,9,15-tetraazabicyclo[9.3.1] pentadeca-1(15),11,13-triene-3,6,9-methylenedi(n-butyl)phosphonate A mixture of 500 mg (2.4 mmol) of 3,6,9,15-tetraazabicyclo[9.3.1]pentadeca-1(15),11,13-triene (prepared by the procedure of Example C), 2.0 g (8 mmol) of tributyl phosphite and 240 mg (8 mmol) of paraformaldehyde was heated at 100° C. with stirring for 1 hr. The resulting viscous solution was concentrated in vacuo to give an oil which was chromatographed on a basic alumina column, eluting with chloroform. After concentration of the organic eluent, the desired product was isolated as a colorless oil, 1.25 g (65%) and characterized by:

$^1$H NMR (CDCl$_3$) δ0.84 (m, 18H), 1.27 (m, 12H), 1.58 (m, 12H), 2.57 (m, 12H), 3.01 (d, 6H), 3.99 (m, 12H), 7.12 (d, 2H), 7.54 (t, 1H); and $^{13}$C NMR (CDCl$_3$) δ13.42, 13.46, 18.50, 18.59, 32.16, 32.43, 49.88, 50.03, 50.16, 50.63, 51.11, 51.27, 52.48, 53.16, 60.71, 60.78, 65.38, 65.48, 65.58, 122.46, 136.96, 157.14; and $^{31}$P NMR (CDCl$_3$) δ24.88 (2P), 24.93 (1 P).

EXAMPLE J

Preparation of 3,6,9,15-tetraazabicyclo[9.3.1] pentadeca-1(15),11,13-triene-3[(4-nitrophenyl) methyl acetate]

To a solution of 2.5 mL of chloroform which was rapidly stirred and 200 mg (0.97 mmol) of 3,6,9,15-tetraazabicyclo [9.3.1]pentadeca-1(15),11,13-triene (prepared by the procedure of Example C), was added in one portion 266 mg (0.97 mmol) of bromo(4-nitrophenyl)methyl acetate in 2.5 mL of chloroform. The reaction mixture was stirred for 24 hrs at room temperature. The solution was concentrated in vacuo to give a semi-solid which was chromatographed on a silica gel column, eluting with chloroform/methanol/ammonium hydroxide (16:4:1). After concentration of the organic eluent, the desired product was isolated as a light yellow solid, 250 mg (64%) and characterized by:

$^{13}$C NMR (CDCl$_3$) δ45.67, 45.90, 45.97, 51.65, 52.08, 52.28, 53.78, 69.54, 119.03, 119.23, 122.85, 130.30, 137.06, 143.27, 147.05, 159.59, 160.41, 171.70.

FINAL PRODUCTS

EXAMPLE 1

Preparation of 3,6,9,15-tetraazabicyclo[9.3.1] pentadeca-1(15),11,13-triene-3,6,9-trimethylenephosphonic acid (PCTMP)

A mixture of 2.06 g (10 mmol) of 3,6,9,15-tetraazabicyclo [9.3.1]pentadeca-1(15),11,13-triene (prepared by the procedure of Example C), 11.3 g (138 mmol) of phosphoric acid and 15 g (152 mmol) of concentrated HCl was heated to gentle reflux (103° C.) with constant stirring followed by the dropwise addition (2 mL/min) of 12.2 g (150 mmol, 15 mL) of aqueous formaldehyde (37%). After complete addition, the reaction mixture was stirred at reflux for 16 hrs, cooled to room temperature and concentrated to a thick, viscous oil. The product was then purified by LC anion exchange chromatography (0–30% formic acid, 3 mL/min, retention time=32 min). The combined fractions were freeze-dried to give 4.8 g (99%) of the title product as a white solid, mp 275°–280° C. and further characterized by:

$^1$H NMR (D$_2$O) δ2.83 (m, 6H), 3.46 (m, 10H), 7.28 (d, 2H), 7.78 (t, 1H); and $^{13}$C NMR (D$_2$O) δ53.61, 53.81, 55.27, 57.93, 62.20, 125.48, 143.08, 152.31; and $^{31}$P NMR (D$_2$O) δ8.12 (2P), 19.81 (1P).

EXAMPLE 2

Preparation of the complex of $^{153}$Sm-3,6,9,15-tetraazabicyclo[9.3.1]pentadeca-1(15),11,13-triene-3, 6,9-trimethylenephosphonic acid ($^{153}$Sm-PCTMP)

A solution of the ligand of Example 1 was prepared by dissolving 3.8 mg of ligand/0.517 mL of deionized water (pH=2). A 1:1 ligand/metal complex was then prepared by combining 40 µl of the ligand solution with 2 mL of aqueous SmCl$_3$·H$_2$O (3×10$^{-4}$M in 0.01N HCl) containing tracer $^{153}$SmCl$_3$. After thorough mixing, the percent metal as a complex was determined by passing a sample of the complex solution through a Sephadex™ column, eluting with 4:1 saline (0.85% NaCl/NH$_4$OH), and collecting 2×3 mL fractions. The amount of radioactivity in the combined elutions was then compared with that left on the resin. Under these conditions, complex was removed with the eluent and non-complexed metal is retained on the resin. By this method complexation was determined to be 98%. A sample of the solution that was passed through the resin was used for pH studies. The pH stability was then determined using the General Procedure above.

EXAMPLE 3

Preparation of 3,9-diacetic acid-6-(methylenephosphonic acid) -3,6,9,15-tetraazabicyclo[9.3.1]pentadeca-1(15),11,13-triene (PC2A1P).

A concentrated hydrochloric acid solution (37%, 5 mL) of 3,9-bis(methylenenitrile)-6-(methylenedimethylphosphonate)-3,6,9,15-tetraazabicyclo [9.3.1]pentadeca-1(15) 11,13-triene (prepared in Example F), 168 mg (1.0 mmol) was heated at reflux for 16 hrs. After cooling, the solution was evaporated to dryness, followed by coevaporation with deionized water (2×10 mL) to remove the excess hydrochloric acid. The filal product was isolated as a dark brown solid upon lyphilization of the concentrated queous solution and characterized by:

$^1$H NMR (D$_2$O) δ2.68 (br s, 4H), 3.31 (br s, 4H), 4.08 (s, 4H), 4.55 (s,4H), 7.16 (d, 2H), 7.68 (t, 1H); and $^{13}$C NMR (D$_2$O) δ52.35, 54.04, 57.02, 59.24, 62.26, 125.52, 143.64, 152.36, 171.54; and $^{31}$P NMR (D$_2$O) δ20.03.

EXAMPLE 4

Preparation of 3,6,9,15-tetraazabicyclo[9.3 1] pentadeca-1(15),11,13-triene-3,6,9-methyleneethylphosphonate tris(potassium salt) (PMEHE)

To an aqueous 0.1N potassium hydroxide solution (2 mL) was added 250 mg (0.38 mmol) of 3,6,9,15-tetraazabicyclo

[9.3.1]pentadeca-1(15),11,13-triene-3,6,9-methylenediethylphosphonate (prepared by the procedure of Example G). The solution was heated at 90° C. for 5 hrs. The reaction mixture was cooled to room temperature, filtered, and freeze-dried to yield the desired product as an off-white solid, 252 mg (97%) and characterized by:

$^{13}$C NMR (D$_2$O) δ18.98, 19.82, 51.78, 52.06, 53.08, 54.46, 54.68, 57.01, 58.22, 60.24, 63.19, 63.25, 63.36, 63.49, 63.59, 63.95, 64.18, 64.25, 66.80, 126.62, 141.63, 159.40; and $^{31}$P NMR (D$_2$O) δ20.58 (s, 2P), 20.78 (s, 1P).

EXAMPLE 5

Preparation of 3,6,9,15-tetraazabicyclo[9.3.1] pentadeca-1(15),11,13-triene-3,6,9-methylene(n-propyl)phosphonate tris(potassium salt) (PMPHE)

To an aqueous solution of potassium hydroxide (0.5 mL of 1N/dioxane (0.5 mL) was added 81 mg (0.108 mmol) of 3,6,9,15-tetraazabicyclo[9.3.1]pentadeca-1(15),11,13-triene-3,6,9-methylenedi(n-propyl)phosphate (prepared by the procedure of Example H). The solution was heated at reflux for 24 hrs. The reaction mixture was cooled to room temperature and extracted with diethyl ether. The ether extract was then concentrated in vacuo to yield the desired product as an off-white solid, 48.6 mg (60%) and characterized by:

$^{31}$P NMR δ20.49 (s, 3P).

EXAMPLE 6

Preparation of 3,6,9,15-tetraazabicyclo[9.3.1] pentadeca-1(15),11,13-triene-3,6,9-methylene(n-butyl)phosphonate tris(potassium salt) (PMBHE)

To an aqueous solution of 35 mL of 1N potassium hydroxide was added 3.21 g (3.88 mmol) of 3,6,9,15-tetraazabicyclo[9.3.1]pentadeca-1(15),11,13-triene-3,6,9-methylenedi(n-butyl)phosphate (prepared by the procedure of Example I). The solution was heated at reflux for 5 days. The reaction mixture was cooled to room temperature, filtered and the filtrate freeze-dried to give a cream colored solid. The solid was then suspended in 150 mL of methanol and stirred for 12 hrs at room temperature. The slurry was then filtered and the filtrate concentrated to give a semi-solid. The solid was taken up in 150 mL of chloroform and dried over anhydrous sodium sulfate and filtered. After concentration in vacuo the product was isolated as an off-white solid, 1.86 g (62%) and characterized by:

$^1$H NMR (D$_2$O) δ0.68 (m, 9H), 1.14 (m, 6H), 1.37 (m, 6H), 2.76 (d, 6H), 3.41 (m, 12H), 3.73 (m, 6H), 7.24 (d, 2H), 7.76 (t, 1H); and $^{13}$C NMR (D$_2$O) δ15.76, 15.80, 21.12, 21.20, 34.96, 35.06, 35.14, 52.08, 52.53, 53.38, 53.48, 54.49, 54.75, 57.70, 57.76, 61.86, 67.65, 67.75, 67.98, 68.08, 125.15, 142.93, 152.25; and $^{31}$P NMR δ9.73 (s, 2P), 21.00 (s, 1P)

EXAMPLE 7

Preparation of 3,6,9,15-tetraazabicyclo[9.3. 1] pentadeca-1(15),11,13-triene-3[(4-nitrophenyl) methyl acetate]-6,9-methylenediethylphosphonate A solution of 250 mg (0.62 mmol) of 3,6,9,15-tetraazabicyclo[9.3.1]pentadeca-1(15),11,13-triene-3[(4-nitrophenyl)methyl acetate] (prepared by the procedure of Example J), 624 mg (3.7 mmol) of triethyl phosphite, and 111 mg (3.7 mmol) of paraformaldehyde was stirred at 100° C. for 1 hr. The resulting homogeneous solution was concentrated in vacuo to give a viscous oil. The oil was dissolved in 10 mL of chloroform and washed with water (3×5 mL). The organic layer was dried over anhydrous magnesium sulfate, filtered and the filtrate concentrated in vacuo to give the product as a viscous oil, 326 mg (96%) and characterized by:

$^{31}$P NMR δ24.67 (s, 2P), 24.88 (s, 1P).

BIODISTRIBUTION

General Procedure

Sprague Dawley rats were allowed to acclimate for five days then injected with 100 μL of the complex solution via a tail vein. The rats weighed between 150 and 200 g at the time of injection. After 30 min. the rats were killed by cervical dislocation and dissected. The amount of radioactivity in each tissue was determined by counting in a NaI scintillation counter coupled to a multichannel analyzer. The counts were compared to the counts in 100 μL standards in order to determine the percentage of the dose in each tissue or organ.

The percent dose in blood was estimated assuming blood to be 7% of the body weight. The percent dose in bone was estimated by multiplying the percent dose in the femur by 25. The percent dose in muscle was estimated assuming muscle to be 43% of the body weight.

In addition to organ biodistribution, chelates of the compounds of Formula (I) were evaluated for efficiency of bone localization since phosphonates are known for their ability to bind to hydroxyapatite.

EXAMPLE I

The percent of the injected dose of complex of Example 2 ($^{153}$Sm-PCTMP) in several tissues are given in Table I. The numbers represent the average of a minimum of 3 rats per data point.

TABLE I

| % INJECTED DOSE IN SEVERAL TISSUES FOR $^{153}$Sm-PCTMP | |
|---|---|
| Tissue | Average |
| Bone | 34.87 |
| Liver | 0.99 |
| Kidney | 1.42 |
| Spleen | 0.07 |
| Muscle | 4.77 |
| Blood | 6.27 |

EXAMPLE II

The percent of the injected dose of complex of Example 5 ($^{153}$Sm-PMPHE) in several tissues are given in Table II. The numbers represent the average of a minimum of 3 rats per data point at 2 hours post injection.

TABLE II

| % INJECTED DOSE $^{153}$Sm-PMPHE (2 hours) | |
|---|---|
| TISSUE | AVERAGE |
| Bone | 10.86 |

TABLE II-continued

| TISSUE | % INJECTED DOSE $^{153}$Sm-PMPHE (2 hours) AVERAGE |
|---|---|
| Liver | 4.14 |
| Kidney | 1.55 |
| Spleen | 0.05 |
| Muscle | 1.19 |
| Blood | 0.25 |
| Heart | 0.08 |
| Lung | 0.12 |
| Brain | 0.00 |
| Stomach | 0.44 |
| Small Intestine | 10.71 |
| Large Intestine | 2.17 |

EXAMPLE III

The percent of the injected dose of complex of Example 6 ($^{153}$Sm-PMBHE) in several tissues are given in Table III. The numbers represent the average of a minimum of 3 rats per data point at 2 hours post injection.

TABLE III

| TISSUE | % INJECTED DOSE $^{153}$Sm-PMBHE (2 hours) AVERAGE |
|---|---|
| Bone | 3.73 |
| Liver | 2.70 |
| Kidney | 0.43 |
| Spleen | 0.05 |
| Muscle | 1.09 |
| Blood | 0.14 |
| Heart | 0.02 |
| Lung | 0.04 |
| Brain | 0.00 |
| Stomach | 0.08 |
| Small Intestine | 57.89 |
| Large Intestine | 0.77 |

EXAMPLE IV

The percent of the injected dose of complex of Example 3 ($^{153}$Sm-PC2A1) in several tissues are given in Table IV. The numbers represent the average of a minimum of 3 rats per data point at 2 hours post injection.

TABLE IV

| TISSUE | % INJECTED DOSE $^{153}$Sm-PC2A1P (2 hours) AVERAGE |
|---|---|
| Bone | 47.98 |
| Liver | 1.46 |
| Kidney | 0.93 |
| Spleen | 0.02 |
| Muscle | 1.00 |
| Blood | 0.36 |
| Heart | 0.04 |
| Lung | 0.06 |
| Brain | 0.01 |
| Stomach | 0.25 |
| Small Intestine | 13.10 |
| Large Intestine | 0.12 |

IMAGING EXPERIMENTS

General Procedure

Injectable solutions were first prepared (0.5M) by dissolving the appropriate amount of each complex in 2 mL of deionized water. The pH of the solutions were then adjusted to 7.4 using 1M HCl or NaOH as needed. The total Gd content of each solution was then determined by ICP analysis.

An anesthetized Sprague Dawley rat was injected intramuscularly with one of the metal solutions described above at a dose of 0.05–0.1 mmol Gd/kg body weight. Images were then taken at various time intervals and compared with a non-injected control at time 0.

EXAMPLE II

The Gd-PCTMP complex (prepared in Example 2) showed kidney enhancement and bone localization in the shoulder, spine and sternum.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. Bicyclopolyazamacrocyclophosphonic acid compounds of the formula

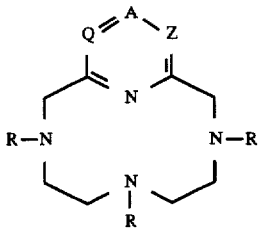

(I)

wherein:

R=—(CH$_2$)$_n$—T where:

n is an integer of 1, 2 or 3;

T is H, C$_1$–C$_{18}$ alkyl, COOH, OH or

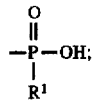

where:

R$^1$ is —OH, C$_1$–C$_5$ alkyl or —O—(C$_1$–C$_5$ alkyl);

with the proviso that at least one T must be P(O)R$^1$OH, wherein R$^1$ is —O—(C$_1$–C$_5$ alkyl);

A, Q and Z independently are CH; or pharmaceutically-acceptable salts thereof.

2. A compound of claim 1 wherein in two R terms T is P(O)R$^1$OH, where R$^1$ is OH, in the third R term T is P(O)R$^1$OH, where R$^1$ is C$_1$–C$_5$ alkyl, and n is 1.

3. A compound of claim 1 wherein in two R terms T is P(O)R$^1$OH, where R$^1$ is OH, in the third R term T is P(O)R$^1$OH, where R$^1$ is —O—(C$_1$–C$_5$ alkyl), and n is 1.

4. A compound of claim 1 wherein in one R term T is P(O)R$^1$OH, where R$^1$ is OH, and in the other two R terms T is P(O)R$^1$OH, where R$^1$ is —O—(C$_1$–C$_5$ alkyl), and n is 1.

5. A compound of claim 1 wherein in one R term T is P(O)R$^1$OH, where R$^1$ is OH, and in the other two R terms T is P(O)R$^1$OH, where R$^1$ is C$_1$–C$_5$ alkyl, and n is 1.

6. A compound of claim 1 wherein in the R term three T equal P(O)R$^1$OH, where R$^1$ is C$_1$–C$_5$ alkyl or —O—(C$_1$–C$_5$ alkyl), and n, R$^1$, A, Q and Z are defined as in claim 1.

7. A compound of claim 6 wherein in the three R terms T is P(O)R$^1$OH, where R$^1$ is —O—(C$_1$–C$_5$ alkyl), and n is 1.

8. A compound of claim 7 wherein in the three R terms T is P(O)R$^1$OH, where R$^1$ is —O—C$_2$H$_5$; and named as 3,6,9,15-tetraazabicyclo[9.3.1]pentadeca-1(15),11,13-triene-3,6,9-methyleneethylphosphonate.

9. A compound of claim 7 wherein in the three R terms T is P(O)R$^1$OH, where R$^1$ is —O—C$_3$H$_7$; and named as 3,6,9,15-tetraazabicyclo[9.3.1]pentadeca-1(15),11,13-triene-3,6,9-methylene(n-propyl)phosphonate.

10. A compound of claim 7 wherein in the three R terms T is P(O)R$^1$OH, where R$^1$ is —O—C$_4$H$_9$; and named as 3,6,9,15-tetraazabicyclo[9.3.1]pentadeca-1(15),11,13-triene-3,6,9-methylene(n-butyl)phosphonate.

11. A compound of claim 6 wherein in the three R terms T is P(O)R$^1$OH, where R$^1$ is C$_1$–C$_5$ alkyl, and n is 1.

* * * * *